United States Patent
Veneman et al.

(10) Patent No.: US 11,072,686 B2
(45) Date of Patent: Jul. 27, 2021

(54) PROCESS FOR PREPARING ETHYLENEAMINE COMPOUNDS

(71) Applicant: NOURYON CHEMICALS INTERNATIONAL B.V., Arnhem (NL)

(72) Inventors: Rens Veneman, Amersfoort (NL); Antoon Jacob Berend Ten Kate, Arnhem (NL); Michiel Jozef Thomas Raaijmakers, Deventer (NL); Slavisa Jovic, Utrecht (NL); Rolf Krister Edvinsson, Partille (SE); Eike Nicolas Kantzer, Uddevalla (SE); Karl Fredrik Lake, Södertälje (SE); Ina Ehlers, Stenungsund (SE); Hendrik Van Dam, Ede (NL)

(73) Assignee: NOURYON CHEMICALS INTERNATIONAL B.V., Arnhem (NL)

( * ) Notice: Subject to any disclaimer, the term of this patent is extended or adjusted under 35 U.S.C. 154(b) by 0 days.

(21) Appl. No.: 16/638,397

(22) PCT Filed: Aug. 7, 2018

(86) PCT No.: PCT/EP2018/071324
§ 371 (c)(1),
(2) Date: Feb. 11, 2020

(87) PCT Pub. No.: WO2019/030194
PCT Pub. Date: Feb. 14, 2019

(65) Prior Publication Data
US 2020/0362111 A1  Nov. 19, 2020

(30) Foreign Application Priority Data

Aug. 11, 2017  (EP) .................................. 17186001

(51) Int. Cl.
  *C07C 209/68*  (2006.01)
  *C08G 73/02*  (2006.01)
  *C07C 213/08*  (2006.01)

(52) U.S. Cl.
  CPC ........ *C08G 73/0213* (2013.01); *C07C 209/68* (2013.01); *C07C 213/08* (2013.01)

(58) Field of Classification Search
  None
  See application file for complete search history.

(56) References Cited

U.S. PATENT DOCUMENTS 2,806,017 A   9/1957  Drechsel
3,383,417 A   5/1968  Lichtenwalter
(Continued)

OTHER PUBLICATIONS

EPO, European Extended Search Report issued in European Application No. 17186001.8, dated Jan. 11, 2018.
(Continued)

*Primary Examiner* — Sudhakar Katakam
*Assistant Examiner* — Jennifer C Sawyer
(74) *Attorney, Agent, or Firm* — Lorenz & Kopf, LLP

(57) ABSTRACT

An integrated process for manufacturing polyethyleneamine compounds selected from the group of polyethyleneamines and hydroxyethylethyleneamines is provided. The process includes in an adduction step, providing a $CO_2$ adduct of a starting compound comprising a $-NH-CH_2-CH_2-NH-$ moiety or a $-NH-CH_2-CH_2-OH$ moiety, or $HO-CH_2-CH_2-OH$, in a reaction step reacting a hydroxy-functional compound selected from the group of ethanolamines and dihydroxyethane with an amine-functional compound, wherein at least part of the total of hydroxy-functional compounds and amine-functional compounds is provided in the form of a $CO_2$ adduct, to form $CO_2$ adduct of a product polyethyleneamine compound, in an elimination step converting $CO_2$ adduct of product polyeth- (Continued)

yleneamine compound to the corresponding product polyethylene amine compound, wherein a fraction comprising a recycle compound comprising a —NH—CH$_2$—CH$_2$—NH— moiety or a —NH—CH$_2$—CH$_2$—OH moiety, or HO—CH$_2$—CH$_2$—OH, or CO$_2$ adducts thereof, is provided from the end of the reaction step or the elimination step to the adduction step or to the reaction step, wherein the recycle compound has per molecule on average fewer of the total of —NH—CH$_2$—CH$_2$—NH— moieties and —NH—CH$_2$—CH$_2$—OH moieties than the product polyethyleneamine compound.

20 Claims, 14 Drawing Sheets

(56) References Cited

U.S. PATENT DOCUMENTS

| | | |
|---|---|---|
| 4,387,249 A | 6/1983 | Harnden et al. |
| 4,503,250 A | 3/1985 | Herdle |
| 7,700,806 B2 | 4/2010 | van Cauwenberge et al. |
| 2009/0240084 A1 | 9/2009 | van Cauwenberge et al. |

OTHER PUBLICATIONS

EPO, International Search Report and Written Opinion issued in International Application No. PCT/EP2018/071324, dated Nov. 20, 2018.
Chen, X. et al., "Synthesis of Novel Polymer/Urea Peptoid Conjugates Using RAFT Polymerization", Macromolecules, 2010, pp. 1341-1348, vol. 43, No. 3.

PROCESS FOR PREPARING ETHYLENEAMINE COMPOUNDS

CROSS-REFERENCE TO RELATED APPLICATION

This application is a U.S. National-Stage entry under 35 U.S.C. § 371 based on International Application No. PCT/EP2018/071324, filed Aug. 7, 2018, which was published under PCT Article 21(2) and which claims priority to European Application No. 17186001.8, filed Aug. 11, 2017, which are all hereby incorporated in their entirety by reference.

TECHNICAL FIELD

The present invention pertains to a method for manufacturing ethyleneamine compounds, in particular polyethyleneamines and hydroxyethylethyleneamines. The invention pertains in particular to an integrated process for preparing these compounds.

BACKGROUND

Ethyleneamines consist of two or more nitrogen atoms linked by ethylene units. Ethyleneamines can be present in the form of linear chains H2N(—CH2-CH2-NH)p-H. For p=1, 2, 3, 4, . . . this gives, respectively, ethylenediamine (EDA), diethylenetriamine (DETA), linear triethylenetetramine (L-TETA), and linear tetraethylenepentamine (L-TEPA). It is clear that this range can be extended. With three or more ethylene units it is also possible to create branched ethyleneamines such as N(CH2-CH2-NH2)3, trisaminoethylamine (TAEA). Two adjacent nitrogen atoms can be connected by two ethylene units to form a piperazine ring —N(-)2-N—. Piperazine rings can be present in longer chains to produce the corresponding cyclic ethyleneamines.

Ethyleneamines, in particular diethylenetriamine (DETA) and higher ethyleneamines are attractive products from a commercial point of view. The term "higher ethyleneamines" refers to ethyleneamines containing three or more ethylene units. In particular, the interest in higher ethyleneamines is increasing as these compounds have numerous commercial applications, e.g., as starting materials for, or use in, asphalt additives, corrosion inhibitors, epoxy curing agents, fabric softeners, fuel additives, hydrocarbon purification, ion exchange resins, lube oil additives, paper wet-strength resins, petroleum production chemicals, solvents, synthetic resins such as polyamide resins, mineral processing aids and interface-active substances (surfactants).

Hydroxyethylethyleneamines find application in chemical processes, as solvent or as reactant. For example, aminoethylethanolamine or AEEA of the formula H2N-CH2-CH2-NH—CH2-CH2-OH is an organic base used in the industrial manufacture of fuel and oil additives, chelating agents, and surfactants. Chain-extended ethanolamines, e.g., monoethanolamine compounds of the formula H2N—(CH2-CH2-NH)q-CH2-CH2-OH, wherein q is 2 or higher, are interesting intermediates for various types of organic synthesis, e.g., the manufacturing of esters of carboxylic acids. They can also be used in, for example, the formation of synthetic resins, as surfactants, for the production of emulsifiers, in fabric softeners, and as epoxy curing agents.

The manufacture of ethyleneamines is presently dominated by two routes, namely the reductive amination of monoethanolamine (MEA) and the ethylene dichloride (EDC) route. The reductive amination of MEA takes place in the presence of a hydrogenation/dehydrogenation catalyst in an excess of ammonia. Next to the reductive amination of MEA to give EDA a number of side reactions, including transamination, produce a mixture of a large number of ethylene and ethanolamines. The output is dominated by mono and diethylene products (EDA, DETA, piperazine (PIP), and AEEA). Higher ethylene and ethanolamines are also formed but the mixture is complex and ineffective in producing high yields of the most important higher ethyleneamines TETA and TEPA.

Several attempts to use transamination to produce ethyleneamines with two or more ethylene units have been reported but seem limited to mainly the diethylene compound DETA.

The EDC route is the substitution reaction of EDC (ethylene dichloride) with ammonia and/or another ethyleneamine at elevated temperatures and pressures to form hydrochlorides which are then reacted with caustic to generate mixtures of ethyleneamines and NaCl. Today, the EDC-based process is the main process for producing higher polyethylenepolyamines. The EDC route is fully dependent on the use of ethylene dichloride which is expensive, difficult to handle, and surrounded by HSE issues. Additionally, the EDC route gives a mixture of many different polyethylenepolyamines, such as is visible in commercially available mixtures of e.g. TETA. Furthermore the EDC route results in the formation of substantial amounts of undesired NaCl which may result in corrosion and the formation of colored products.

Various processes for manufacturing hydroxyethylethyleneamines have been described.

For example, U.S. Pat. No. 3,383,417 describes the manufacture of aminoethylethanolamine by reaction of monoethanolamine with itself in the presence of a catalyst comprising nickel, copper, and a minor amount of chromium oxide, manganese oxide, molybdenum oxide, and thorium oxide.

U.S. Pat. No. 7,700,806 describes a process for preparing ethyleneamines and ethanolamines by hydrogenative amination of monoethyleneglycol and ammonia in the presence of a catalyst. The process is carried out in two stages, wherein in the first stage the amination is carried out over a hydroamination catalyst to a monoethyleneglycol conversion of not more than 40%, and in the second stage the reaction is carried out over a supported catalyst comprising ruthenium and cobalt with a specific particle shape.

U.S. Pat. No. 4,387,249 discloses the reaction of ethylenediamine (EDA), ethanolamine (MEA) and urea to give aminoethylethyleneurea (UDETA) and ethyleneurea (EU) which after hydrolysis with NaOH (aq) gives diethylenetriamine (DETA) and ethylenediamine (EDA).

U.S. Pat. No. 4,503,250 describes a process for preparing linear polyalkylene polyamines which comprises reacting ammonia or an alkyleneamine compound having two primary amino groups or mixtures thereof with an alcohol or an alkanolamine compound having a primary amino group and a primary or secondary hydroxy group or mixtures thereof in the presence of a derivative of carbonic acid at a temperature at which the reaction will proceed under pressures sufficient to maintain the reaction mixture substantially in a liquid phase. The process results in the formation of urea adducts of polyalkylene polyamines. The urea adducts are converted to polyethylene polyamines by reaction with 50% aqueous KOH under reflux overnight. 8 moles KOH are used per mole carbon dioxide.

Nowadays there is a high demand for higher ethylene amine compounds. Hence, there is a need for a process for selectively making such higher compounds in an effective and industrially attractive manner. The present invention provides such a process.

BRIEF SUMMARY

An integrated process is provided for manufacturing polyethyleneamine compounds selected from the group of polyethyleneamines and hydroxyethylethyleneamines. The process includes in an adduction step providing a CO2 adduct of a starting compound comprising a —NH—CH2-CH2-NH— moiety or a —NH—CH2-CH2-OH moiety, or HO—CH2-CH2-OH, in a reaction step reacting a hydroxy-functional compound selected from the group of ethanolamines and dihydroxyethane with an amine-functional compound, wherein at least part of the total of hydroxy-functional compounds and amine-functional compounds is provided in the form of a CO2 adduct, to form CO2 adduct of a product polyethyleneamine compound, in an elimination step converting CO2 adduct of polyethyleneamine compound to a corresponding product polyethyleneamine compound, wherein a fraction comprising a recycle compound comprising a —NH—CH2-CH2-NH— moiety or a —NH—CH2-CH2-OH moiety, or HO—CH2-CH2-OH, or CO2 adducts thereof, is provided from the end of the reaction step or the elimination step to the adduction step or to the reaction step, wherein the recycle compound has per molecule on average fewer of the total of —NH—CH2-CH2-NH— moieties and —NH—CH2-CH2-OH moieties than the product polyethyleneamine compound.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

In certain embodiments, numbers in this description indicating amounts, ratios of materials, physical properties of materials, and/or use are may be understood as being modified by the word "about". The term "about" as used in connection with a numerical value and the claims denotes an interval of accuracy, familiar and acceptable to a person skilled in the art. In general, such interval of accuracy is ±10%.

The present invention makes it possible to manufacture ethylene amine compounds in an effective and industrially attractive manner. Though the product of the process is called product polyethylene amine, throughout this document it is also understood that there can be multi-constituent products and even multiple products in this product polyethyleneamine. Furthermore as should also be clear from the embodiments, a product polyethyleneamine may contain hydroxyl groups. Further advantages of the present invention and specific embodiments thereof will become apparent from the further specification.

In its simplest form, the overall reaction underlying the process according to the invention can be exemplified by the reaction of ethylenediamine (EDA) with monoethanolamine (MEA) to form diethylenetriamine (DETA) and water:

H2N—CH2-CH2-NH2+HO—CH2-CH2-NH2→
H2N—CH2-CH2-NH—CH2-CH2-NH2+H2O.

However, ethylenediamine and monoethanolamine do not react directly. They can be made reactive by converting either compound into a CO2 adduct, with release of water. Though many CO2 adducts are cyclic ureas or cyclic carbamates, a CO2 adduct moiety in many embodiments more in general covers a moiety wherein two nitrogen atoms, or a nitrogen atom and an oxygen atom, or two oxygen atoms, are connected through a —C(O)— moiety. Hence, they can also be linear between nitrogen and/or oxygen atoms of two different molecules. Furthermore CO2 can also form an adduct with an amine or alcohol in a terminal single sided group, linked to only one nitrogen or oxygen atom. One CO2 adduct of ethylenediamine is ethylene urea. One CO2 adduct of monoethanolamine is 2-oxazolidone, also indicated herein as CMEA. This is an example of the adduction step of the process according to the invention.

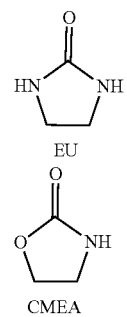

EU

CMEA

Ethylenediamine can then be reacted with CMEA to form a CO2 adduct of DETA, also indicated herein as UDETA, and water. The same product can be obtained by reacting EU with MEA.

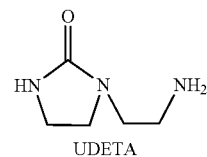

UDETA

The CO2 adduct of UDETA can then be converted to DETA in an elimination step. This can, e.g., be effectuated by reaction with water with concurrent formation of CO2.

As will be clear to the skilled person, the process can be applied analogously by reacting longer ethyleneamine compounds and/or longer hydroxy-functional compounds than EDA and/or CMEA as starting materials. The use of hydroxy-functional compounds with one hydroxy group will result in the formation of ethyleneamine compounds. The use of hydroxy-functional compounds with two hydroxy groups, e.g. monoethylene glycol/dihydroxyethane (HO—CH2-CH2-OH) or diethanolamine (HO—CH2-CH2-NH—CH2-CH2-NH2) will result in the formation of hydroxyethylethyleneamines, which can in turn be converted to polyethyleneamines.

The process as depicted above looks deceptively simple. It has been found that performing such process in commercial practice in an efficient manner is quite complicated. The present invention provides an efficient way to perform this process.

The first step in the process of the present invention is an adduction step, in which a CO2 adduct is provided of a starting compound comprising a —NH—CH2-CH2-NH— moiety or a —NH—CH2-CH2-OH moiety, or HO—CH2-CH2-OH. The adduction step can be carried out in various manners.

In one embodiment, the adduction step comprises the step of reacting gaseous CO2 with a starting compound comprising a —NH—CH2-CH2-NH— moiety or a —NH-CH2-CH2-OH moiety, or HO—CH2-CH2-OH, resulting in the formation of the respective CO2 adducts. This step is also indicated herein as the absorption step.

In another embodiment of the adduction step, the CO2 adduct is formed by reaction of a starting compound comprising —NH-CH2-CH2-NH— moiety or a —NH-CH2-CH2-OH moiety, or HO—CH2-CH2-OH with a compound not being CO2 which can transfer a carbonyl group to the starting compounds, resulting in the formation of CO2 adducts thereof. These compounds can be indicated as carbon oxide delivering agents.

Carbon oxide delivering agents other than CO2 within the scope of the present invention include organic compounds in which a carbonyl moiety is available for being transferred as described above. Organic compounds in which a carbonyl moiety is available include urea and derivatives thereof; linear and cyclic alkylene ureas, especially cyclic ethylene urea, mono or di-substituted alkylene ureas, alkyl and dialkyl ureas, linear and cyclic carbamates, organic carbonates and derivatives or precursors thereof. Such derivatives or precursors may for example include ionic compounds such as carbonate or bicarbonate salts, carbamic acids and associated salts, that can be converted, in some embodiments in situ in the process of the invention, into their non-ionic counterparts, for example into linear and cyclic carbamate or urea compounds. When such ionic compounds are used in the present invention, they are organic hydrocarbon-based carbonate, bicarbonate or carbamate salts. Preferably the CO delivering agent is CO2 or an organic compound that is suitable for use as a carbon oxide delivering agent and wherein alkylene is ethylene, or urea or ethylene carbonate, more preferably the carbon oxide delivering agent is at least partly added as carbon dioxide or urea. The carbon oxide delivering agent can be present in the process in the same molecule as the amine functional or the ethanolamine functional compound by using the aforementioned urea or carbamate compounds.

Examples of Carbon Oxide Delivering Agents Include

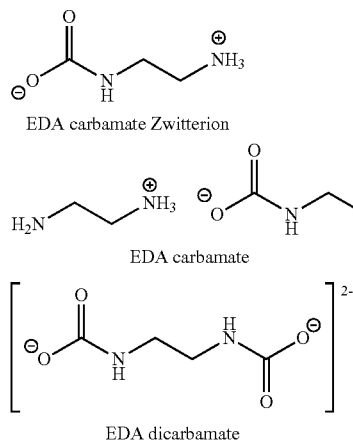

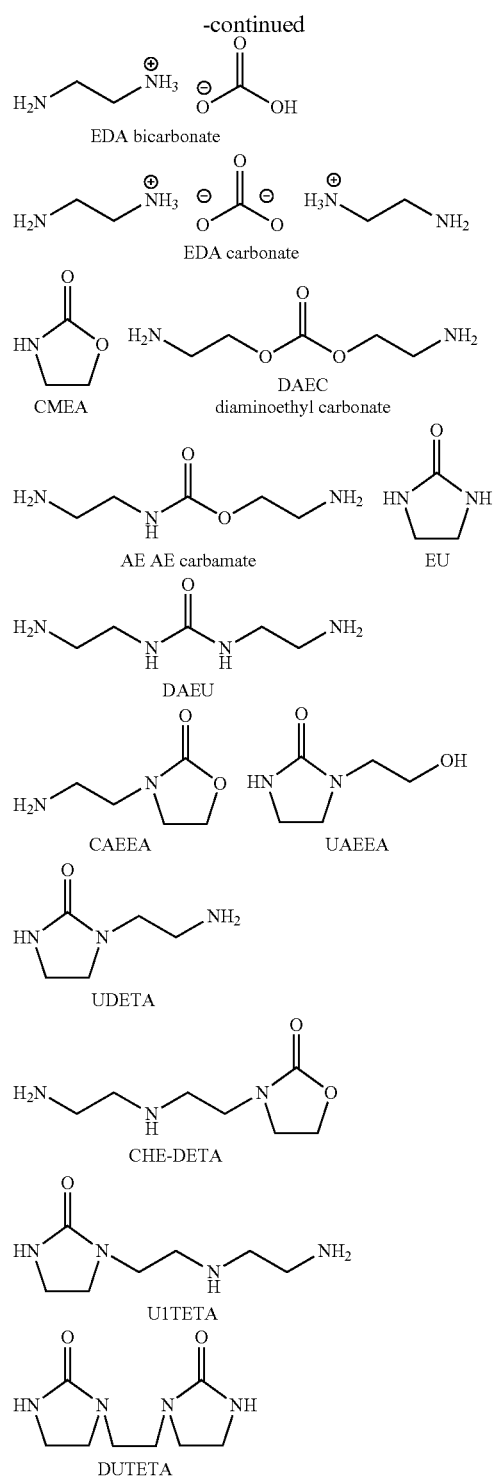

In the above drawing CAEEA again stands for the carbamate of aminoethylethanolamine, UDETA for the urea of diethylene triamine, DAEU stands for diaminoethyl urea, AE AE carbamate stands for amino ethyl aminoethanol carbamate, CHE-DETA stands for the carbamate of hydroxyethyldiethylene triamine, U1TETA stands for the terminal urea of triethylene tetramine, and DUTETA stands for the 1,3-diurea of triethylene tetramine.

The carbon oxide delivering agent is most preferably added to the reaction in the form of carbon dioxide, urea, the carbamate derivative of the ethanolamine-functional compound or the urea derivative of the amine-functional compound, or a combination of these.

The embodiment of the adduction step in which the $CO_2$ adduct is formed by reaction of a starting compound comprising —NH—CH2-CH2-NH— moiety or a —NH—CH2-CH2-OH moiety, or HO—CH2-CH2-OH with a compound not being $CO_2$ which can transfer a carbonyl group to the starting compounds, can also be indicated as a $CO_2$ transfer step.

In the reaction step of the process according to the invention a hydroxy-functional compound selected from the group of ethanolamines and dihydroxyethane with an amine-functional compound, wherein at least part of the total of hydroxy-functional compounds and amine-functional compounds is provided in the form of a $CO_2$ adduct, to form $CO_2$ adduct of a product polyethyleneamine compound.

In the elimination step of the process according to the invention the $CO_2$ adduct of polyethyleneamine compound is converted to the corresponding polyethylene amine compound. It is called an elimination step because the carbonyl group is eliminated from the molecule.

There are various ways to carry out the elimination step.

In one embodiment, the elimination step comprises the step of reacting the $CO_2$ adduct of polyethyleneamine compound with water to form $CO_2$ and the corresponding ethylene amine compound. This embodiment is also indicated herein as a desorption step.

In another embodiment the elimination step is carried out by reacting the $CO_2$ adduct of polyethyleneamine compound with an inorganic base, resulting in the formation of a polyethyleneamine compound and a carbonate salt. This step is also indicated herein as a caustic treatment step. Within the context of the present invention, an inorganic base is a Lewis or Brønsted base which does not contain carbon-carbon bonds. In many embodiments the inorganic base contains a metal, alkalimetal or alkaline earth metal cation, and in many embodiments it is a Brønsted base. Preferably the inorganic base is a strong inorganic base which is a base that does not contain carbon-carbon bonds and has a pKb of less than 1.

In another embodiment, the elimination step is carried out by transferring the carbonyl group from the $CO_2$ adduct of the polyethyleneamine compound to a compound having a —NH—CH2-CH2-NH— moiety or a NH—CH2-CH2-OH moiety, or HO—CH2-CH2-OH. This step is also indicated as a $CO_2$ transfer step.

In the present specification, the adduction step is indicated as the step in which a $CO_2$ adduct of a starting compound comprising a —NH—CH2-CH2-NH— moiety or a —NH—CH2-CH2-OH moiety, or HO—CH2-CH2-OH is formed, while the reaction step is indicated as the step in which a hydroxy-functional compound is reacted with an amine-functional compound, wherein at least part of the total of hydroxy-functional compounds and amine-functional compounds is provided in the form of a $CO_2$ adduct, to form $CO_2$ adduct of a product polyethyleneamine compound, and the elimination step is the step in which the $CO_2$ adduct of product polyethyleneamine compound is converted to the corresponding product polyethylene amine compound. As will be clear to the skilled person, depending on the reaction conditions, some reaction may also take place in the adduction step, and elimination may also take place during the reaction step. In particular, during the reaction step carbonyl groups may be transferred from the $CO_2$ adduct of the product polyethyleneamine compound to a compound having a —NH—CH2-CH2-NH— moiety or a NH—CH2-CH2-OH moiety, or HO—CH2-CH2-OH.

It is a feature of the present invention that a fraction comprising a recycle compound comprising a —NH—CH2-CH2-NH— moiety or a —NH—CH2-CH2-OH moiety, or HO—CH2-CH2-OH, or $CO_2$ adducts thereof, is provided from the end of the reaction step or the elimination step, or a separation step, to the adduction step or to the reaction step, the recycle compound having per molecule on average fewer of the total of —NH—CH2-CH2-NH— moieties and —NH-CH2-CH2-OH moieties than the product polyethyleneamine compound.

In one embodiment, the recycle compound is the starting compound comprising a —NH—CH2-CH2-NH— moiety or a —NH—CH2-CH2-OH moiety, or HO—CH2-CH2-OH, or a $CO_2$ adduct thereof. In another embodiment the recycle compound is an intermediate product. Of course, the recycled fraction can comprise both starting compounds and intermediate compounds.

It is noted that the present application describes numerous streams from one step to another step. Except when explicitly indicated otherwise it is possible to provide the stream from one step to the other in its entirety or in part. Where it is indicated that a compound is provided from one step to the other, other compounds may also be present in the stream provided from one step to the other.

BRIEF DESCRIPTION OF THE DRAWINGS

The present invention will hereinafter be described in conjunction with the following drawing figures, wherein like numerals denote like elements, and.

The following is noted with respect to the figures:

The figures are intended to illustrate the invention. This invention is not limited thereto or thereby.

Embodiments of various figures can be combined unless they are mutually exclusive.

The figures are flow sheets illustrating the process according to the invention. The figures do not present a reactor set up. For example, the absorption step, the reaction step, and the desorption step indicated as three different steps in the figures can be carried out sequentially in a single vessel. By the same token, the various lines are intended to show how components flow from one reaction step to the other. They do not represent real-life structures.

The figures do not always show all elements of the process according to the invention.

The figures do not show all purge streams or make-up streams that may be present in the practical performance of the process according to the invention although, as will be evident to the skilled person, purge streams and make-up streams may be necessary in practice to maintain stable operation.

DETAILED DESCRIPTION

The following detailed description is merely exemplary in nature and is not intended to limit the invention or the application and uses of the invention. Furthermore, there is no intention to be bound by any theory presented in the preceding background of the invention or the following detailed description.

As will be evident to the skilled person, the three steps of the process according to the invention will also not be completely separate in that some reaction can take place during the adduction step and during the elimination step, depending on the prevailing process conditions and medium composition. This does not detract from the description of the individual steps described herein.

Figure 1:
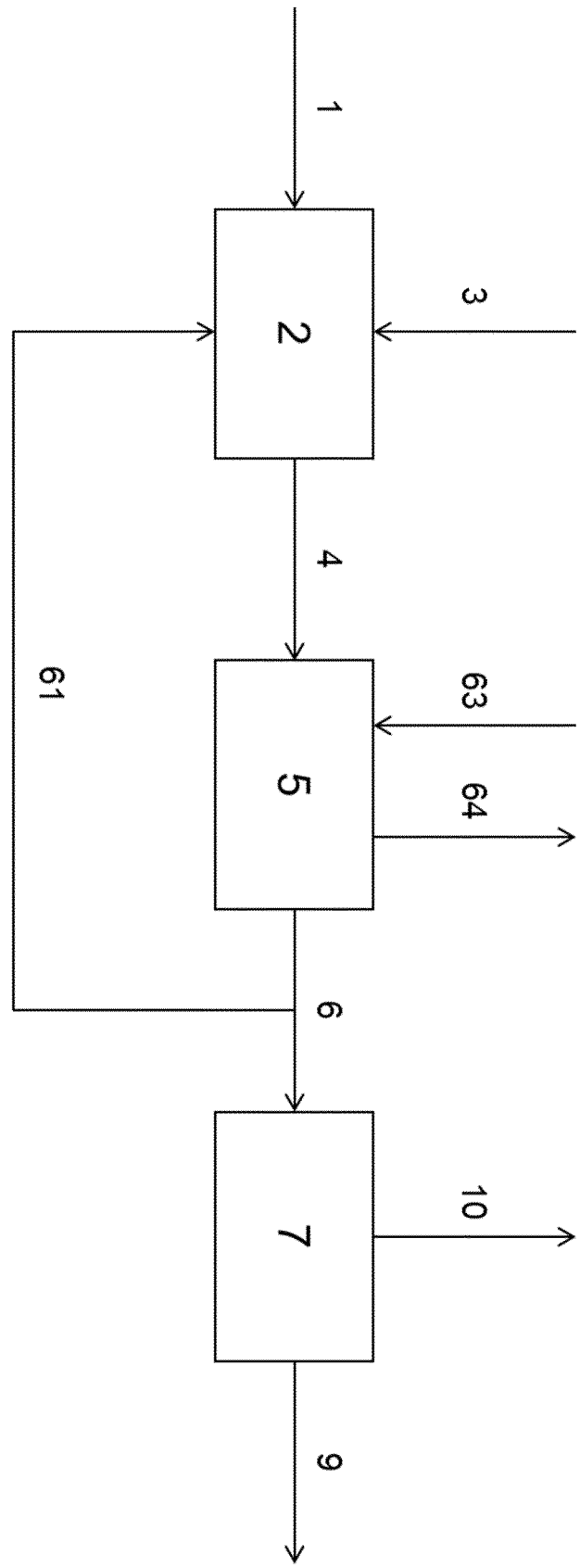
FIG. 1 shows an example of the basis of the process according to an embodiment described herein.

FIG. 1 shows an example of the basis of the process according to the invention. A starting compound comprising a —NH—CH2-CH2-NH— moiety or a —NH—CH2-CH2-OH moiety, or HO—CH2-CH2-OH is provided through line 1 to an adduction step 2, where it is combined with CO2 or another carbon oxide delivering agent provided through line 3 to form a CO2 adduct of the starting compound. A stream comprising the CO2 adduct is provided through line 4 to a reaction step 5, where it is reacted with a further reactant (already present, provided through inlet not shown, or provided from the adduction step 2), the reactants in the reaction step being a hydroxy-functional compound selected from the group of ethanolamines and monoethyleneglycol and an amine-functional compound, wherein at least part of the total of hydroxy-functional compounds and amine-functional compounds is provided in the form of a CO2 adduct derived from step 2. In reaction step 5 a CO2 adduct of a product polyethyleneamine compound is formed, which is provided through line 6 to an elimination step 7. A fraction comprising a recycle compound comprising a —NH—CH2-CH2-NH— moiety or a —NH-CH2-CH2-OH moiety, or HO—CH2-CH2-OH, or CO2 adducts thereof, is provided through line 61 from, in this case, the end of the reaction step to, in this case, the adduction step. In elimination step 7, CO2 adduct of polyethyleneamine compound is converted to the corresponding ethylene amine compound, which is withdrawn through line 9. The compound comprising the carbonyl group, eliminated from the CO2 adduct of the product polyethyleneamine compound is withdrawn through line 10. Line 63 and Line 64 are optional and allow for the removal and dosing of compounds before, after or during reaction. Compounds that could be removed or dosed include CO2, H2O, amine functional compounds and/or urea derivatives thereof.

Figure 1A:
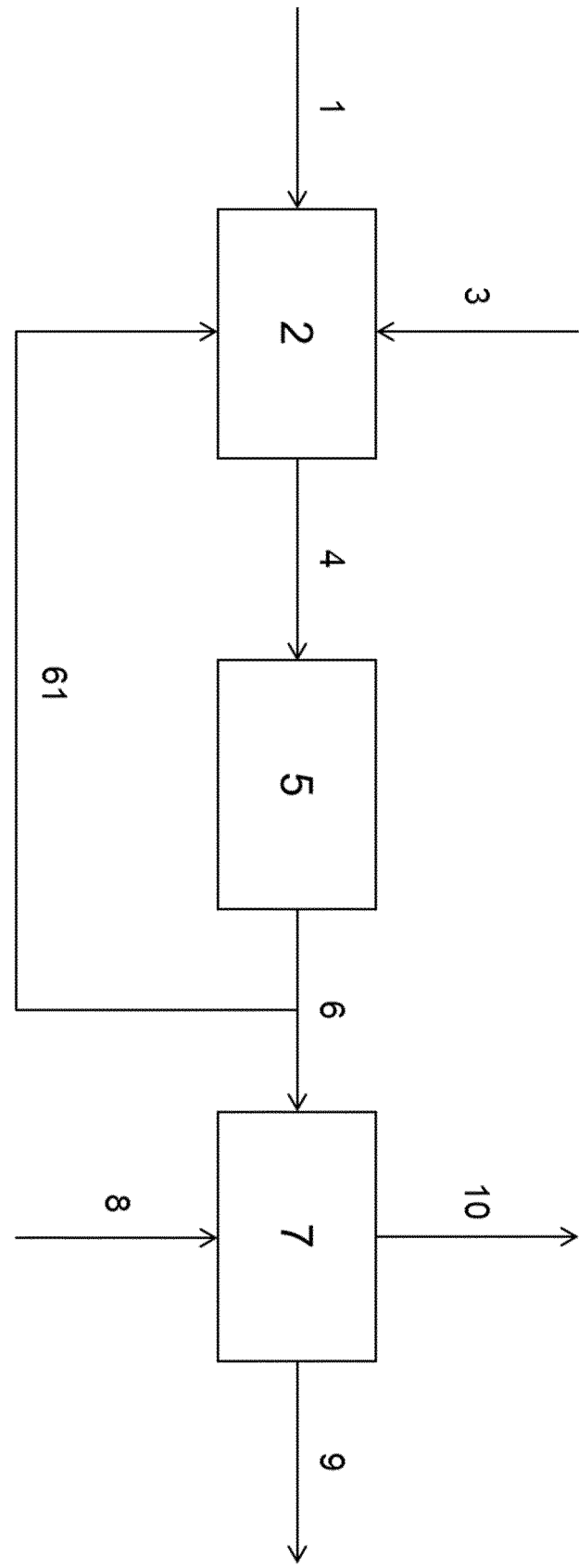
FIG. 1A shows an example of the basis of the process according to a further embodiment described herein, wherein the adduction step is an absorption step in which $CO_2$ is absorbed in a reaction medium and the elimination step is a desorption step in which the $CO_2$ adduct of the product polyethyleneamine compound is reacted with water to form the corresponding ethylene amine compound and $CO_2$.

In a preferred embodiment of the present invention, the adduction step is an absorption step in which CO2 is absorbed in a reaction medium comprising a starting compound comprising a —NH—CH2-CH2-NH— moiety or a —NH—CH2-CH2-OH moiety, or HO—CH2-CH2-OH to form a CO2 adduct of said starting compound and the elimination step is a desorption step in which the CO2 adduct of the product polyethyleneamine compound is reacted with water to form the corresponding ethylene amine compound and CO2. This embodiment is illustrated in FIG. 1A. In FIG. 1A starting compound comprising a —NH—CH2-CH2-NH— moiety or a —NH—CH2-CH2-OH moiety, or HO—CH2-CH2-OH is provided through line 1 to an absorption step 2 where it is combined with CO2 provided through line 3 and reacted to form a CO2 adduct of the starting compound. The CO2 adduct is provided through line 4 to a reaction step 5, where it is reacted with a further reactant, the reactants in the reaction step being a hydroxy-functional compound selected from the group of ethanolamines and dihydroxyethane and an amine-functional compound, wherein at least part of the total of hydroxy-functional compounds and amine-functional compounds is provided in the form of a CO2 adduct derived from step 2. In reaction step 5 a CO2 adduct of a product polyethyleneamine compound is formed, which is provided through line 6 to a desorption step 7. In desorption step 7 a stripping gas can be provided through line 8, and a stripping gas containing CO2 is removed through line 10. The resulting polyethyleneamine compound is withdrawn through line 9, and can be processed as desired. A fraction comprising a recycle compound comprising a —NH—CH2-CH2-NH— moiety or a —NH—CH2-CH2-OH moiety, or HO—CH2-CH2-OH, or CO2 adducts thereof, is provided through line 61 from, in this case, the end of the reaction step to, in this case, the adduction step.

The stripping gas used in the process according to the invention can have any desired composition. It can contain inert gases such as nitrogen or noble gases to create volume and stripping action. The presence of water may be regulated in that steam can be attractive to provide stripping action and heat to the process. On the other hand, as water is consumed in the desorption step and produced in the reaction step and the adduction step, regulating the water content in the gas streams in the process according to the invention enables steering of the reaction steps. The presence of compounds which interfere with the reaction, or the presence of which may generate undesirable side effects is preferably limited. For example, it is preferred to limit the presence of oxygen in the process according to the invention, as this may result in color formation. Therefore, gases and liquids such as water used in the process according to the invention may be subjected to an oxygen removal step, should this be desired.

In one embodiment of the present invention CO2 formed in the desorption step is provided at least in part to the absorption step.

Figure 2:
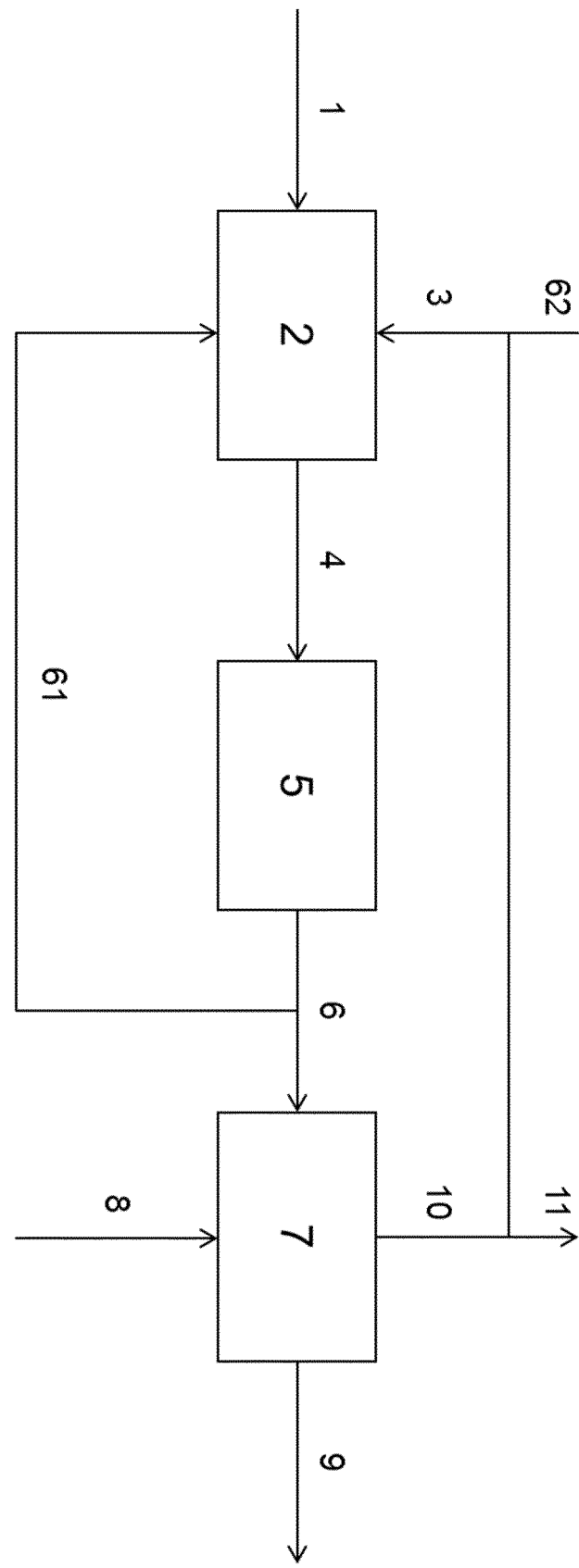
FIG. 2 shows an example of a process according to a further embodiment described herein, wherein $CO_2$ formed in the desorption step is provided at least in part to the absorption step.

One embodiment of this option is depicted in FIG. 2, where the CO2 provided through line 3 to absorption step 2 is derived from the desorption step through line 10. As it may be desired not to recycle all CO2, a separate line 11 branches off from line 10. Line 62 is optional. It allows for the addition of additional CO2 to compensate for losses.

In a further embodiment of the present invention stripping gas withdrawn from the desorption step is subjected to a CO2 removal step and recycled at least in part to the desorption step.

Figure 3:
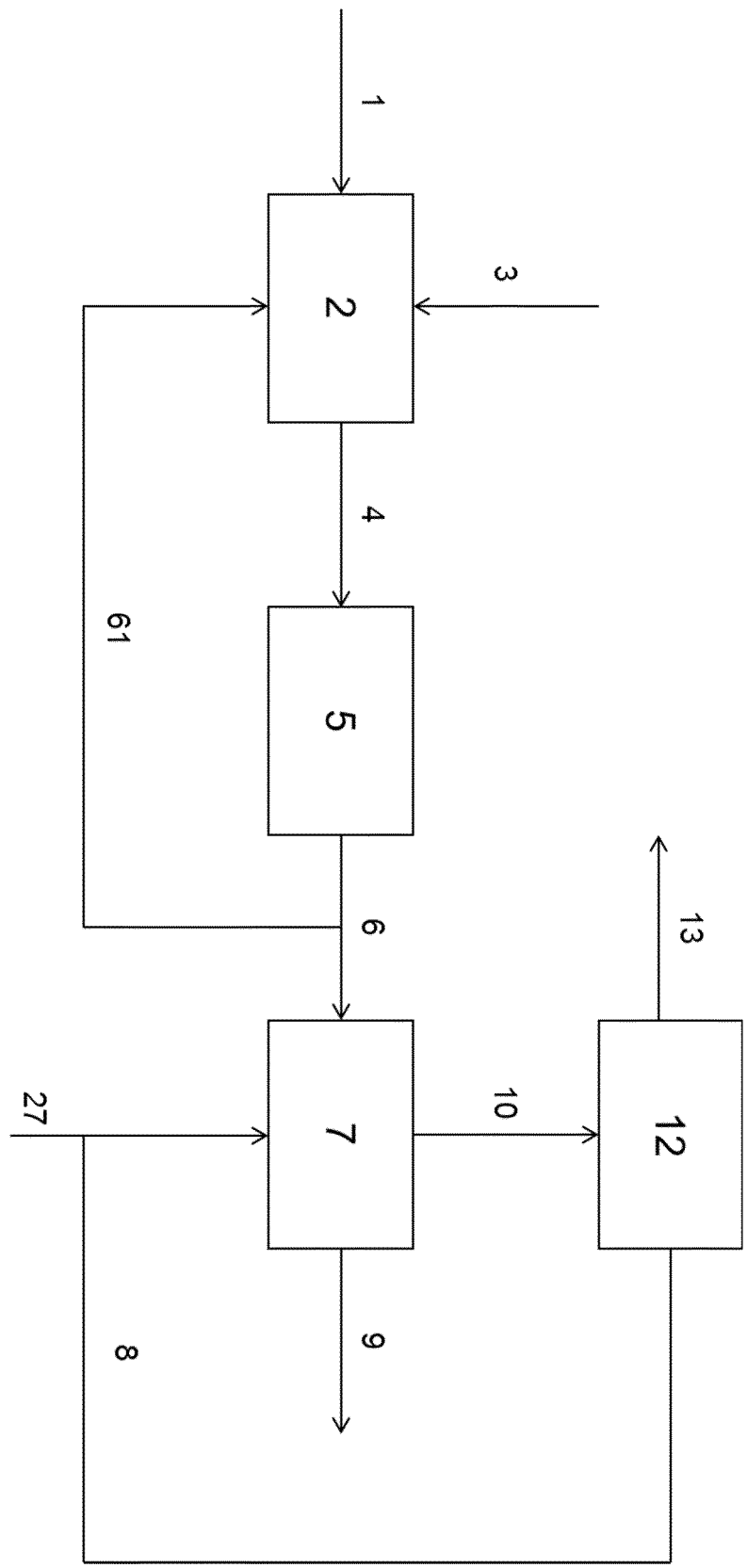

One embodiment of this option is illustrated in FIG. 3, where the CO2-containing stripping gas in line 10 is provided to a CO2 removal step 12. The stripping gas is withdrawn through line 8 and recycled to the desorption step 7. CO2 is withdrawn through line 13. Line 27 is optional. It allows for the addition of N2 to compensate for losses.

Figure 4:
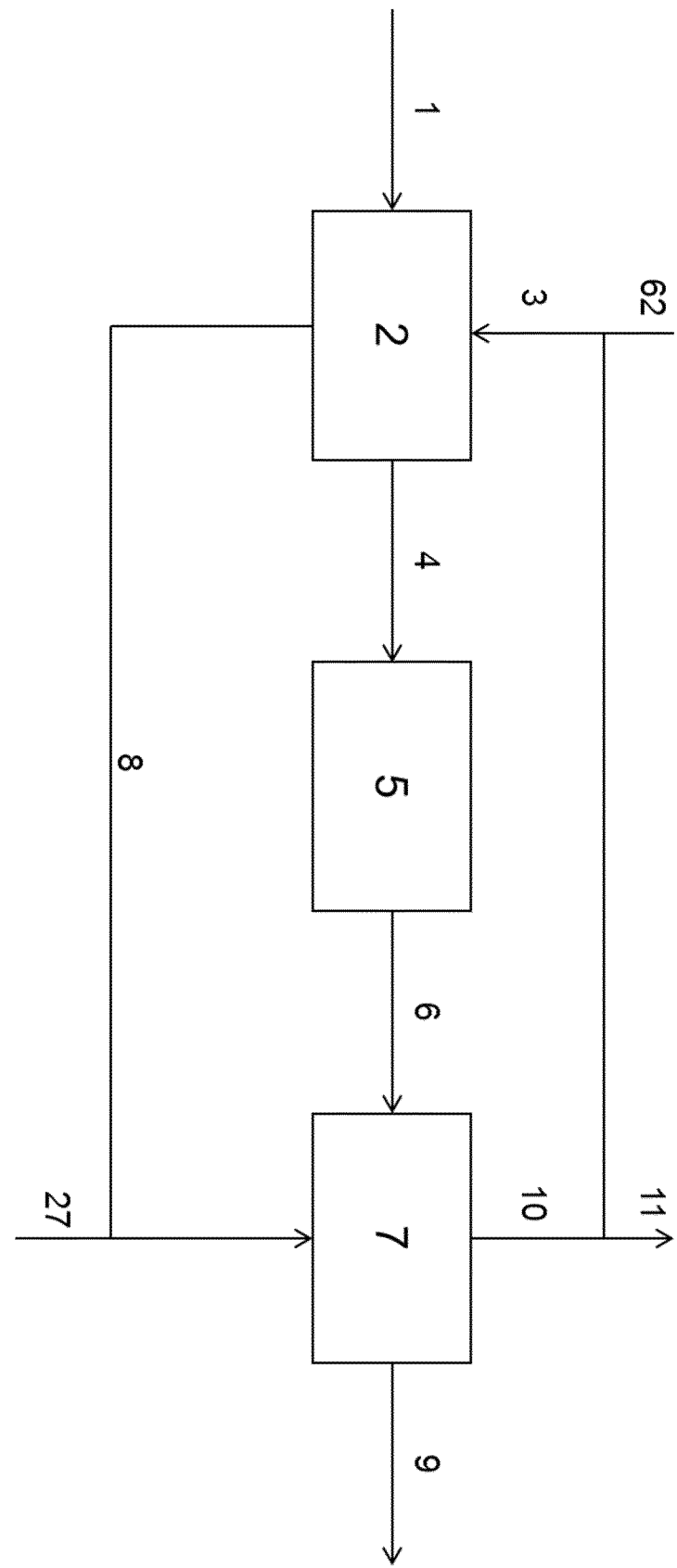
FIG. 4 shows an example of a process according to a further embodiment in which allows for the addition of $CO_2$ to compensate for losses.

Another embodiment of this option is illustrated in FIG. 4, where the absorption step is used to remove CO2 from the stripping gas. In FIG. 4, as in FIG. 2, stripping gas containing CO2 is removed from the desorption step 7 through line 10 and provided to the absorption step through line 3. Line 62 is optional. It allows for the addition of CO2 to compensate for losses. In absorption step 2, CO2 is absorbed from the CO2-containing stripping gas. Stripping gas from which CO2 has been removed is withdrawn from the absorption step and provided through line 8 to desorption step 7. Line 27 is optional. It allows for the addition of stripping gas to compensate for losses.

Figure 5:
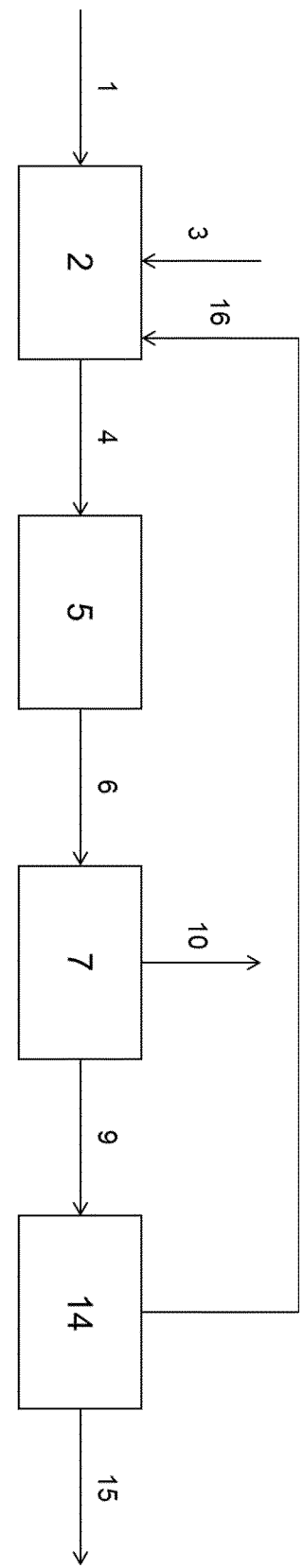
FIG. 5 shows a further embodiment of a process, wherein a separation step is provided after the elimination step.

FIG. 5 shows a further embodiment of the present invention, wherein a separation step 14 is provided after the elimination step. The separation step 14 results in the separation of recycle compounds, e.g., starting materials and/or intermediate compounds which are withdrawn through line 16 and are, in the illustrated embodiment, provided to the adduction step 2. They can also be provided to the reaction step (not shown in this Figure). The separation step 14 also yields a product fraction of higher ethyleneamine compounds which is withdrawn through line 15.

Figure 6:
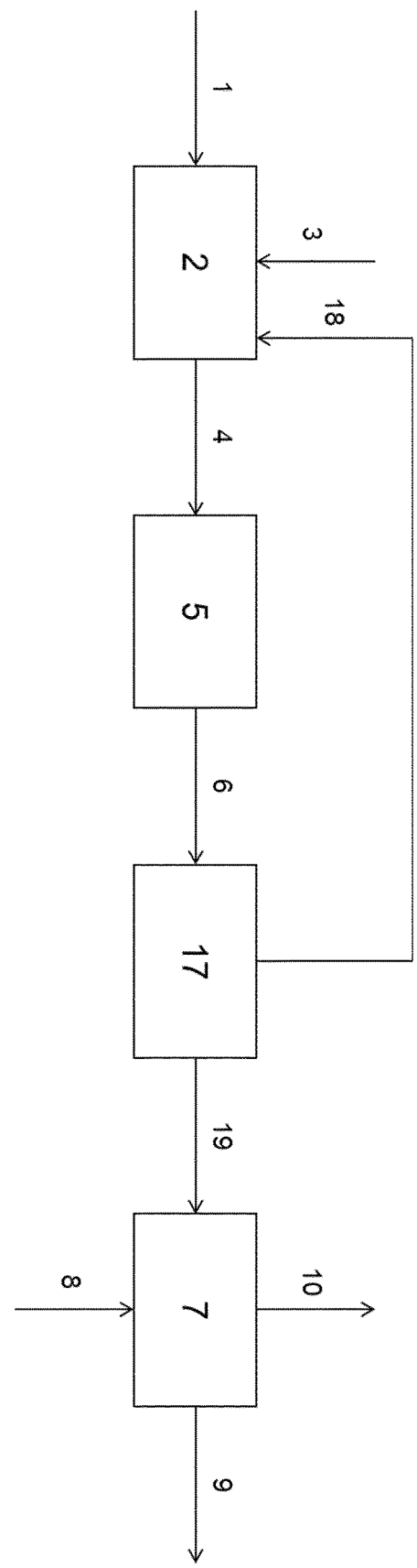
FIG. 6 shows a further embodiment of a process in which a separation step is provided after the reaction step and before the elimination step.

Another embodiment of this option is illustrated in FIG. 6. In this embodiment a separation step 17 is provided after the reaction step and before the elimination step. In this separation step recycle compounds, e.g., starting materials or CO2 adducts thereof, or intermediate compounds or CO2 adducts thereof, are separated from the CO2 adduct of product polyethyleneamine compounds, and provided through line 18 to, in this case, the adduction step 2. They can also be provided to the reaction step 5 (not shown). The CO2 adduct of the polyethyleneamine compound is provided through line 19 to elimination step 7.

In one embodiment of the present invention, the elimination step comprises a first elimination step and a further elimination step, wherein the first elimination step and the further elimination step are independently selected from the group of
  a desorption step in which the CO2 adduct of polyethyleneamine compound is reacted with water to form CO2 and the corresponding polyethylene amine compound,
  a caustic treatment step in which CO2 adduct of polyethyleneamine compound is reacted with an inorganic base, resulting in the formation of a polyethyleneamine compound and a carbonate salt, and
  a CO2 transfer step, wherein the carbonyl group from the CO2 adduct of the polyethyleneamine compound is transferred to a compound having a —NH—CH2-CH2-NH— moiety or a NH—CH2-CH2-OH moiety, or HO—CH2-CH2-OH,
wherein the first elimination step converts part of the CO2 adducts of polyethyleneamines present in the feed thereto into the polyethyleneamine compounds, while part of the CO2 adducts of polyethyleneamines present in the feed to the first elimination step is not converted in the first elimination step, and is provided to the second elimination step. Of course, provision of further elimination steps is also possible.

It may be preferred for the first elimination step to be a desorption step or a CO2 transfer step and the further elimination step to be a desorption step or a caustic treatment step, wherein the steps are not the same. Examples of suitable combinations are: desorption followed by caustic treatment and desorption in combination with recycle, optionally with caustic treatment for specific fractions.

In one embodiment the elimination step comprises a desorption step in which not all CO2 adducts are converted to polyethyleneamine compounds. Thus, the product provided from the desorption step 7 to the separation step may still comprise CO2 adducts of polyethyleneamine compounds. If this is the case, it has been found that the CO2 adducts are generally CO2 adducts of higher polyethyleneamine compounds rather than CO2 adducts of lower-boiling starting materials. In this case, separation step 14 results in the separation of recycle compounds, in particular starting materials, which are withdrawn through line 16, a product fraction of higher polyethyleneamine compounds which is withdrawn through line 15, and a fraction comprising CO2 adducts of higher polyethyleneamine compounds. This latter fraction is withdrawn from separation step 14 through line 20. It can be processed in various manners, which are illustrated in FIGS. 7A, 7B, 7C, and 7D.

Figure 7A:
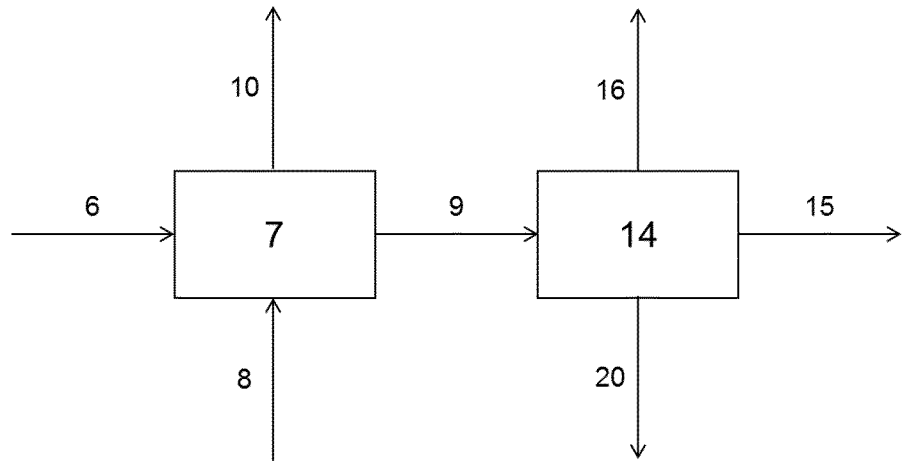
FIGS. 7A, 7B, 7C, and 7D show further various embodiments for separating and processing fractions comprising $CO_2$ adducts of higher polyethyleneamine compounds.

In FIG. 7A, the CO2 adduct of higher polyethyleneamine compounds withdrawn through line 20 is not subjected to a further elimination step, but processed as such. It can be subjected to further purification or separation steps (not shown).

Figure 7B:
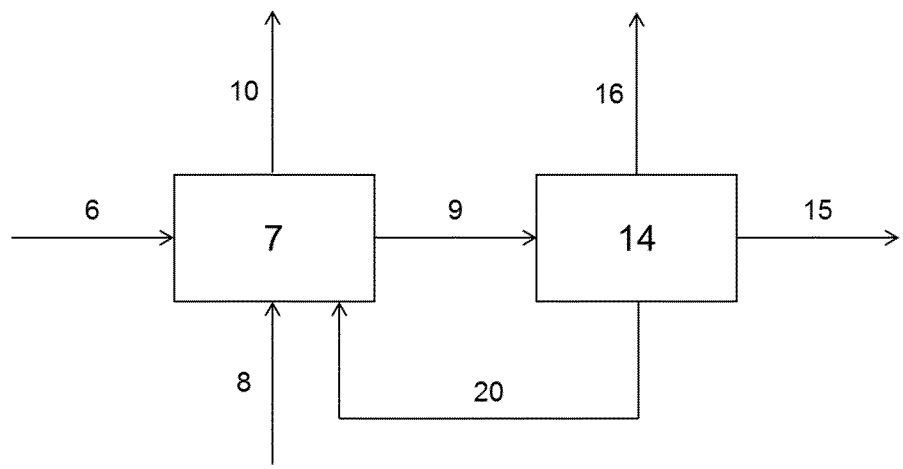

In FIG. 7B, the CO2 adduct of higher polyethyleneamine compounds withdrawn through line 20 is recycled to the desorption step 7.

Figure 7C:
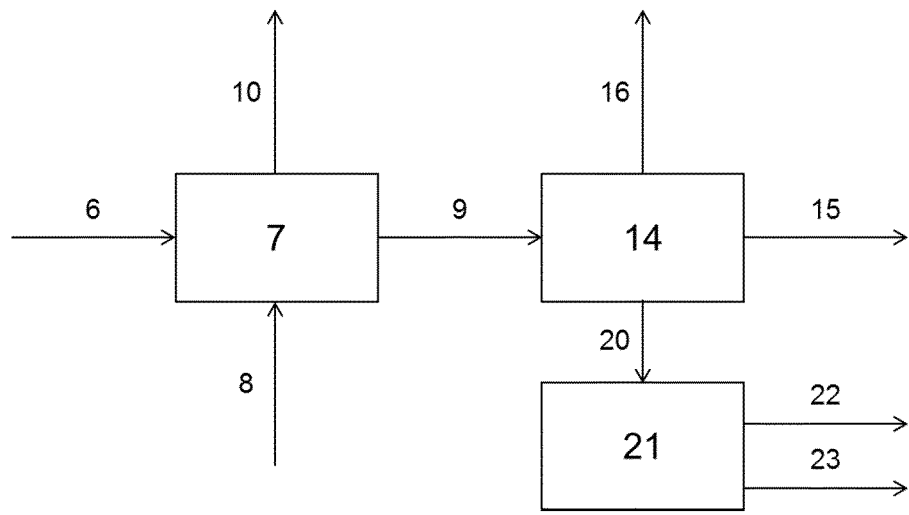

In FIG. 7C the CO2 adduct of higher polyethyleneamine compounds withdrawn through line 20 is provided to a further elimination step 21. In this further elimination step 21, step, more stringent conditions apply than in desorption step 7. While desorption step 7 is carried out with water with release of CO2, further elimination step 21 can be carried in different manners, e.g. using a (strong) inorganic base. Further elimination step 21 yields a product fraction of polyethyleneamine compounds withdrawn through line 22 and a waste fraction withdrawn through line 23. If elimination step 21 is a treatment with (strong) inorganic base, the waste fraction is a salt fraction.

Figure 7D:
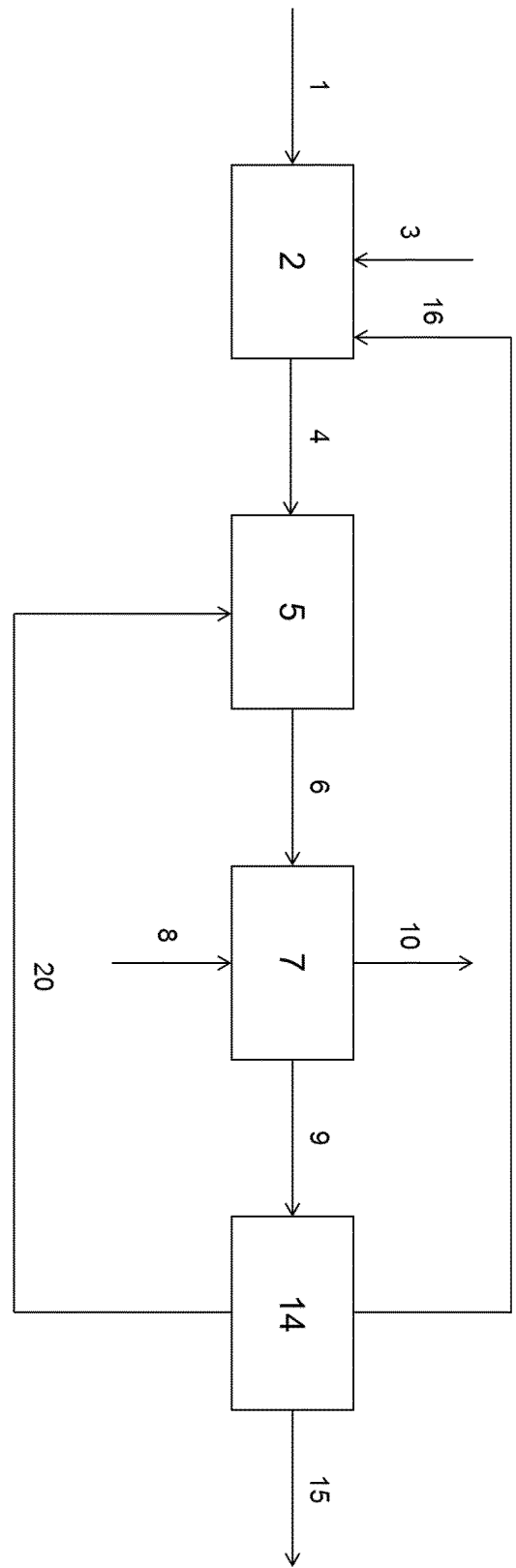

In FIG. 7D the CO2 adduct of higher polyethyleneamines or hydroxyethylethyleneamines withdrawn through line 20 is provided, at least in part, back to reaction step 5.

It is noted that FIGS. 7A, 7B, and 7C do not show the entire process of the present invention.

In general, waste fractions generated in the process according to the invention, whether they are water, salt, or organic fractions, can be treated as desired. In one embodiment they are combined with waste fractions from other plants, and processed in a single unit, e.g., a waste water purification unit. In another embodiment, waste product, e.g., a heavy organic fraction, is provided to a purification unit where it is separated into further products. It can also be provided as starting material to further reactors, where, if so desired it can be combined with other starting materials. Purification of desired product can be carried out in dedicated runs. It is also possible to combine product obtained in the process according to the invention with product obtained in other processes, or in other runs of the process according to the invention, and subject the combined product to a purification step.

Conventional purification steps of product fractions or waste fractions can be applied as desired. They include contaminant removal by, e.g., one or more of absorption, selective extraction, product distillation, filtration, and other steps known to the skilled person.

As will be evident to the skilled person, and as is conventional in chemical industry, heat generated in one step can be used as energy source in other steps. The same goes for water and steam (as is described elsewhere herein).

Figure 8A:
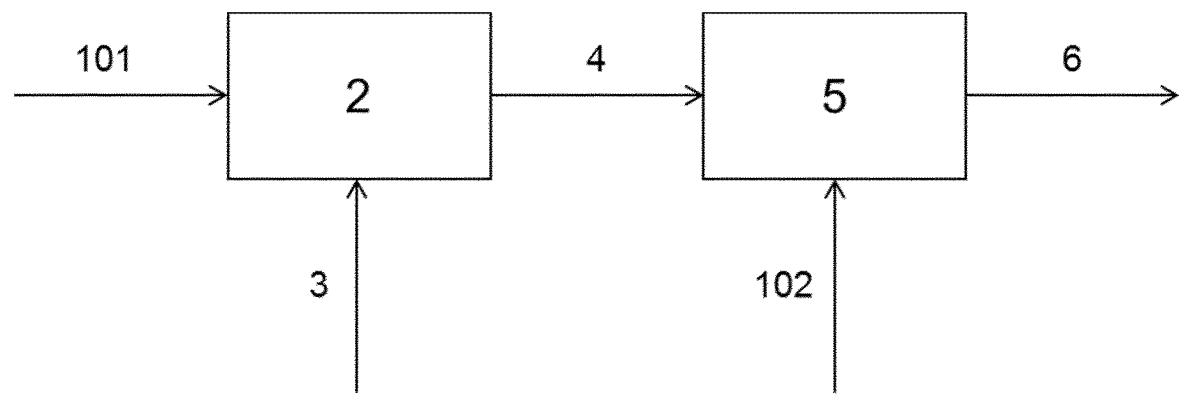
FIGS. 8A, 8B, and 8C show further various embodiments for providing amine compounds or hydroxy-functional compounds for adduction or adduction and reaction steps.
Figure 8B:
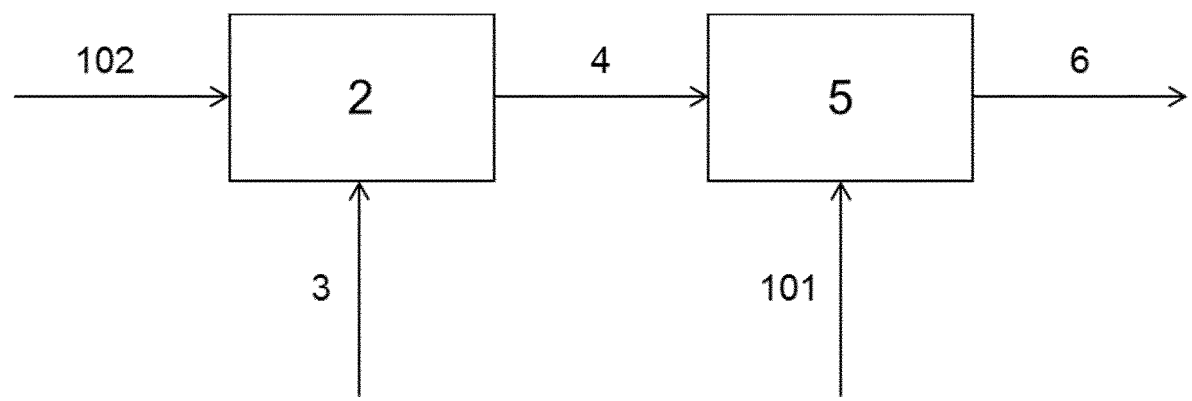
Figure 8C:
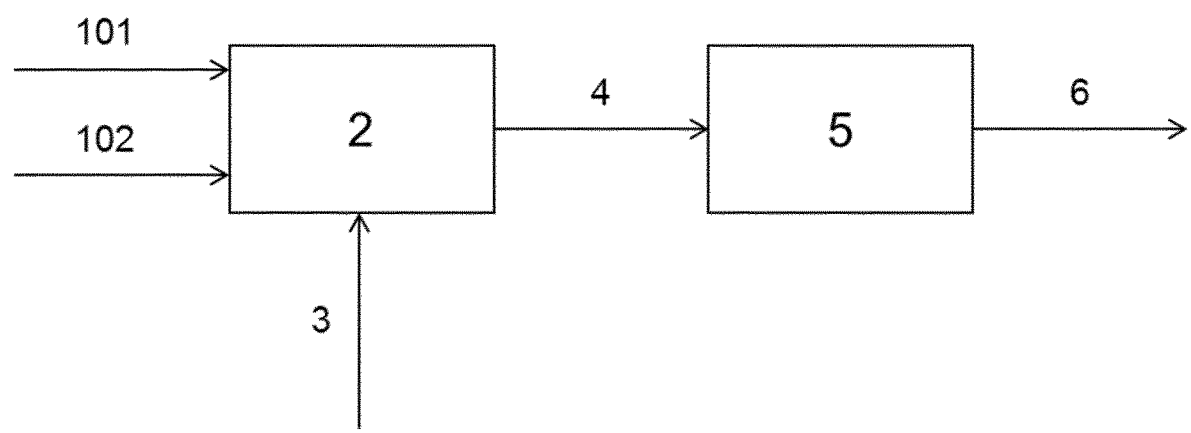

In the reaction step of the process according to the invention, a hydroxy-functional compound selected from the group of ethanolamines and dihydroxyethane is reacted with an amine-functional compound, wherein at least part of the total of hydroxy-functional compounds and amine-functional compounds is provided in the form of a $CO_2$ adduct. Thus, in one embodiment, the amine-compound is provided in its entirety or in part in the form of a $CO_2$ adduct. In this case, the amine compound will be provided in its entirety or in part to the adduction step where it is converted into its $CO_2$ adduct, which is then provided to the reaction step, with the hydroxy-functional compound being provided to the reaction step. This embodiment is illustrated in FIG. 8A, where an amine compound is provided to the adduction step through line 101 and hydroxy-functional compound is provided to the reaction step through line 102. FIG. 8B illustrates the reverse option, where a hydroxy-functional compound is provided to the adduction step through line 102 and amine-functional compound is provided to the reaction step through line 101. The most attractive option may be the option where both the amine-functional compound and the hydroxy-functional compound are provided to adduction step 2. This embodiment is illustrated in FIG. 8C. In this Figure, the compounds are provided through separate lines 101 and 102. Obviously, the compounds can be provided in combination through a single line.

It is noted that FIGS. 8A, 8B, and 8C do not show the entire process of the present invention.

In the reaction step, water is produced. If so desired, water from the reaction step can be provided to the elimination step, in particular where the elimination step is a desorption step or a caustic treatment, which generally also takes place in the presence of water.

Figure 9:
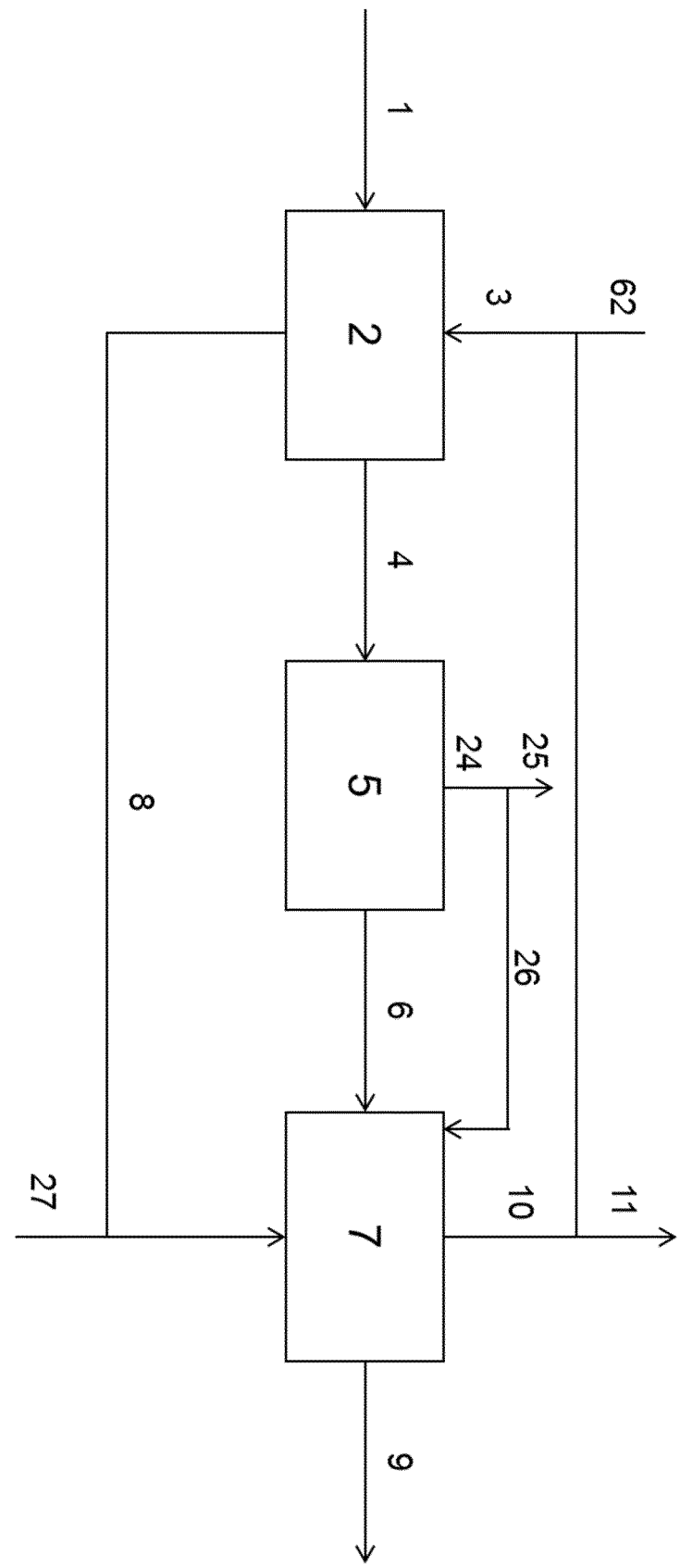
FIG. 9 shows an embodiment of the process in which water is withdrawn from a reaction step and is provided to desorption step.

In the adduction step, a starting compound comprising a —NH—CH2-CH2-NH— moiety or a —NH—CH2-CH2-OH moiety, or HO—CH2-CH2-OH is converted into the $CO_2$ adduct of said starting compound. If the adduction step is an absorption step, $CO_2$ is consumed in this step and water is produced. Conversely, in the desorption step a $CO_2$ adduct of an amine is converted into the amine in the presence of water. In this reaction water is consumed and $CO_2$ is produced. In one embodiment of the present invention, a stream comprising $CO_2$ is withdrawn from the desorption step and provided to the absorption step and a stream comprising water is withdrawn from the absorption step and provided to the desorption step. Water is also produced in the reaction step. Therefore, in one embodiment a stream comprising water is withdrawn from the reaction step and provided to the desorption step. FIG. 9 illustrates these steps. In FIG. 9, line 10 is a $CO_2$-containing stripping gas steam which is provided to the absorption step 2. Line 62 is optional. It allows for the addition of $CO_2$ to compensate for losses. Line 8 is a water (e.g. steam)-containing stripping gas stream withdrawn from the absorption step 2 and provided to desorption step 7. Line 27 is optional. It allows for the addition of stripping gas to compensate for losses. Line 24 is a water stream derived from reaction step 5, which is provided at least in part to desorption step 7 through line 26. Line 25 is a purge for the case that not all water is to be recycled.

If so desired, a separation step can be carried out between the reaction step and the elimination step and after the elimination step. In one embodiment, the elimination step is a desorption step. One embodiment of this option is illustrated in FIG. 10.

Figure 10:
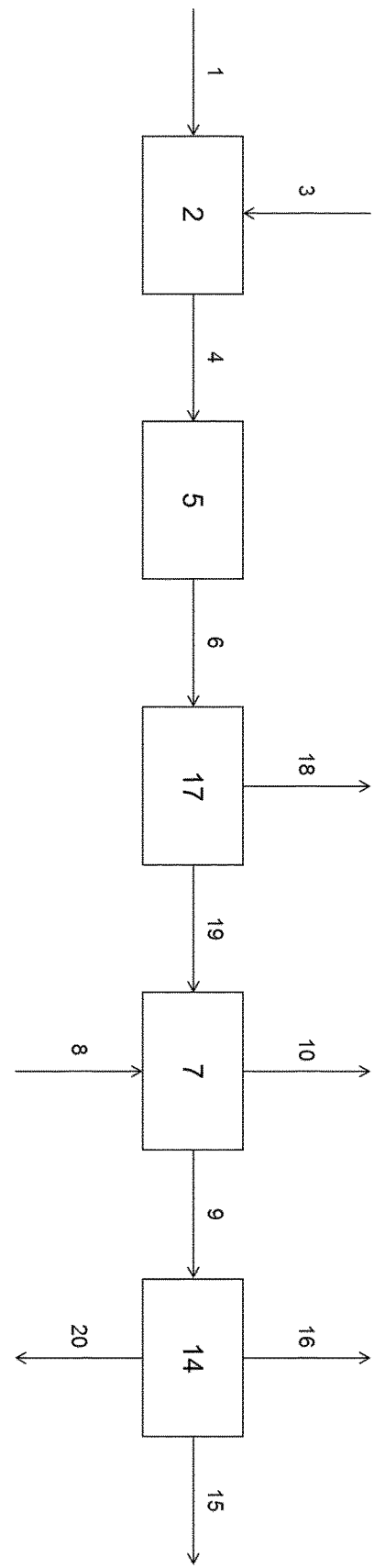
FIG. 10 shows an embodiment of the process in which a separation step is provided after the reaction step and before the desorption step.

In FIG. 10, a separation step 17 is provided after the reaction step and before the desorption step. In this separation step, recycle compounds or $CO_2$ adducts thereof, e.g., starting materials or $CO_2$ adducts thereof, are separated from the $CO_2$ adduct of the product polyethyleneamine compound and withdrawn through line 18. They are provided, at least in part, to absorption step 2 or reaction step 5 (not shown). The $CO_2$ adduct of polyethyleneamine compound is provided through line 19 to desorption step 7. A further separation step 14 is provided after desorption step 7. In this case separation step 14 results in the separation of a product fraction of higher ethyleneamine compounds which is withdrawn through line 15, and a fraction comprising $CO_2$ adducts of higher polyethyleneamine compound, withdrawn through line 20. This fraction can be processed as desired, e.g., as discussed in the context of FIG. 7 above. Lighter compounds such as starting materials and intermediates may, if formed and if so desired, be withdrawn through line 16 and recycled to the adduction step 2 or reaction step 5 (recycle not shown).

As indicated above, embodiments of various figures can be combined unless they are mutually exclusive. Some preferred combinations are presented in the following figures.

Figure 11:
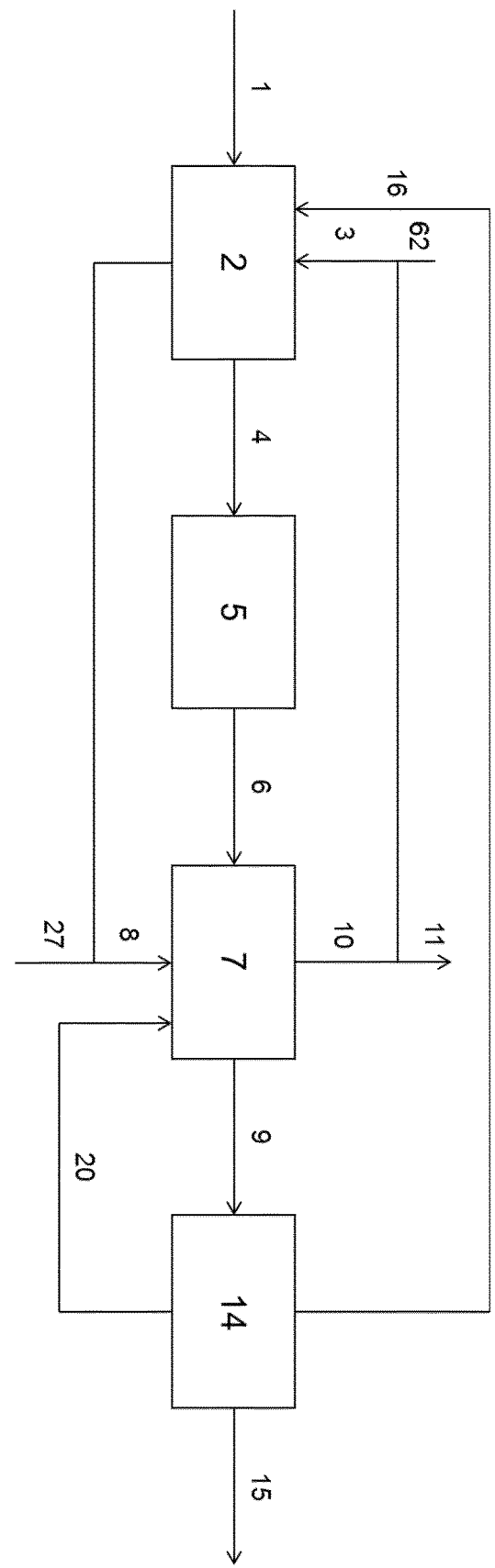
FIGS. 11 and 12 show further specific embodiments of the process.

FIG. 11 illustrates a preferred embodiment of the present invention, which is a combination of the embodiments of FIGS. 4, 5, and 7b.

In FIG. 11 a starting compound comprising a —NH—CH2-CH2-NH— moiety or a —NH—CH2-CH2-OH moiety, or HO—CH2-CH2-OH is provided through line 1 to an absorption step 2 where it is combined with $CO_2$ provided through line 3 and reacted to form a $CO_2$ adduct. Line 62 is optional. It allows for the addition of $CO_2$ to compensate for losses. The $CO_2$ adduct is provided through line 4 to a reaction step 5, where it is reacted with a further reactant, the reactants in the reaction step being a hydroxy-functional compound selected from the group of ethanolamines and dihydroxyethane and an amine-functional compound, wherein at least part of the total of hydroxy-functional compounds and amine-functional compounds is provided in the form of a $CO_2$ adduct derived from step 2. In reaction step 5 a $CO_2$ adduct of a product polyethyleneamine compound is formed, which is provided through line 6 to a desorption step 7. In desorption step 7 a stripping gas is provided through line 8, and a stripping gas containing $CO_2$ is removed through line 10 and provided to absorption step 2. In absorption step 2, $CO_2$ is absorbed from the $CO_2$-containing stripping gas. Stripping gas from which $CO_2$ has been removed is withdrawn from the absorption step and provided through line 8 to desorption step 7. Line 27 can provide additional stripping gas if this is required.

The resulting polyethyleneamine compound is withdrawn through line 9 and provided to a separation step 14. Separation step 14 results in the separation of starting materials which are withdrawn through line 16 and are provided to the absorption step 2. They can also be provided to the reaction step (not shown in this Figure). The separation step 14 also yields a product fraction of higher ethyleneamine compounds which is withdrawn through line 15, and a fraction comprising CO2 adducts of higher polyethyleneamine compounds. This latter fraction is withdrawn from separation step 14 through line 20 and recycled back to the desorption step.

Figure 12:
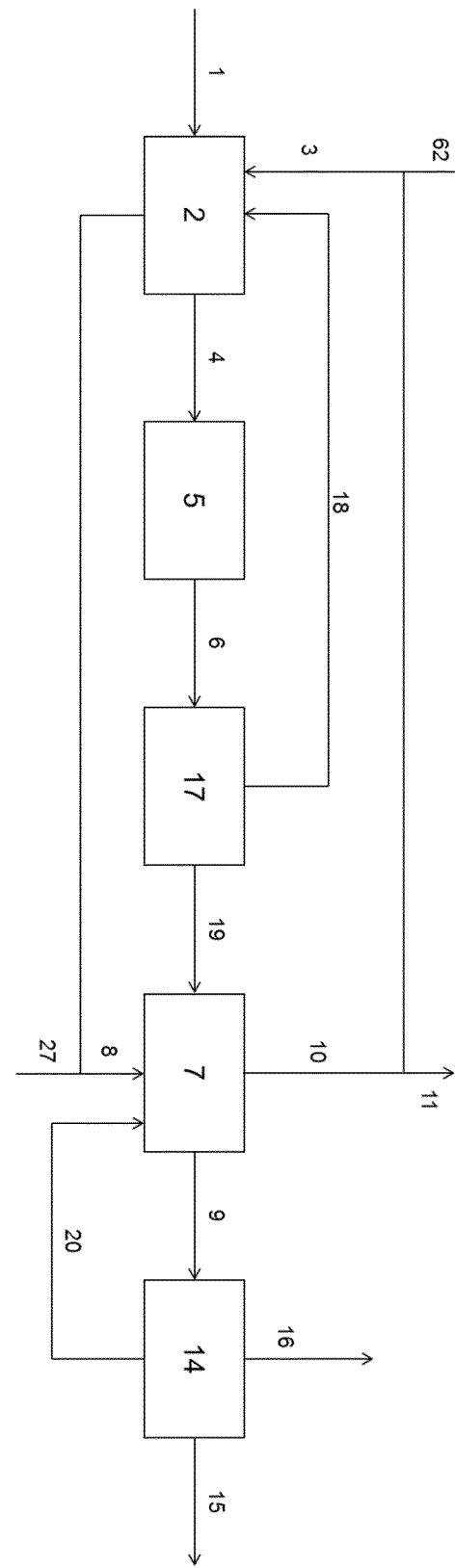

FIG. 12 illustrates another preferred embodiment of the present invention.

In FIG. 12 a starting compound comprising a —NH—CH2-CH2-NH— moiety or a —NH—CH2-CH2-OH moiety, or HO—CH2-CH2-OH is provided through line 1 to an absorption step 2 where it is combined with CO2 provided through line 3 and reacted to form a CO2 adduct. Line 62 is optional. It allows for the addition of CO2 to compensate for losses. The CO2 adduct is provided through line 4 to a reaction step 5, where it is reacted with a further reactant, the reactants in the reaction step being a hydroxy-functional compound selected from the group of ethanolamines and dihydroxyethane and an amine-functional compound, wherein at least part of the total of hydroxy-functional compounds and amine-functional compounds is provided in the form of a CO2 adduct derived from step 2. In reaction step 5 a CO2 adduct of a polyethyleneamine compound is formed, which is provided through line 6 to a separation step 17. In this separation step starting materials or CO2 adducts thereof are separated from the CO2 adduct of product polyethyleneamine compound, and provided through line 18 to, in this case, the absorption step 2. They can also be provided to the reaction step 5. The CO2 adduct of polyethyleneamine compound is provided through line 19 to desorption step 7. In desorption step 7 a stripping gas is provided through line 8, and a stripping gas containing CO2 is removed through line 10 and provided to absorption step 2. In absorption step 2, CO2 is absorbed from the CO2-containing stripping gas. Stripping gas from which CO2 has been removed is withdrawn from the absorption step and provided through line 8 to desorption step 7. The resulting polyethyleneamine compounds are withdrawn through line 9 and provided to a separation step 14. Separation step 14 yields a product fraction of higher ethyleneamine compounds which is withdrawn through line 15, and a fraction comprising CO2 adducts of polyethyleneamine compounds This latter fraction is withdrawn from separation step 14 through line 20 and recycled back to the desorption step. Lighter compounds such as starting materials and intermediates may, if formed and if so desired, be withdrawn through line 16 and recycled to the adduction step 2 or reaction step 5 (recycle not shown). Line 27 can provide additional CO2 if this is required.

The various steps will be elucidated in more detail below.

Starting Compounds and Reaction Products

The invention is directed to a process for manufacturing ethylene amine compounds selected from polyethyleneamine compounds and hydroxyethylethylene compounds. They are obtained from the reaction of a hydroxy-functional compound selected from the group of ethanolamines and dihydroxyethane and amine-functional compounds.

Preferred amine-functional compounds include ethylenediamine (EDA), N-methylethylenediamine (MeEDA), diethylenetriamine (DETA), piperazine (PIP), N-aminoethylpiperazine (AEP), triethylene tetramine (TETA), N,N'-diaminoethylpiperazine (DAEP), tetraethylenepentamine (TEPA), and pentaethylenehexamine (PEHA).

Preferred hydroxy-functional compounds include ethanolamine (MEA), aminoethylethanolamine (AEEA), hydroxyethyl-diethylenetriamine (HE-DETA), hydroxyethyltriethylenetetraamine (HE-TETA), and diethanolamine.

Some structures of the amine and hydroxy-functional compound are provided below

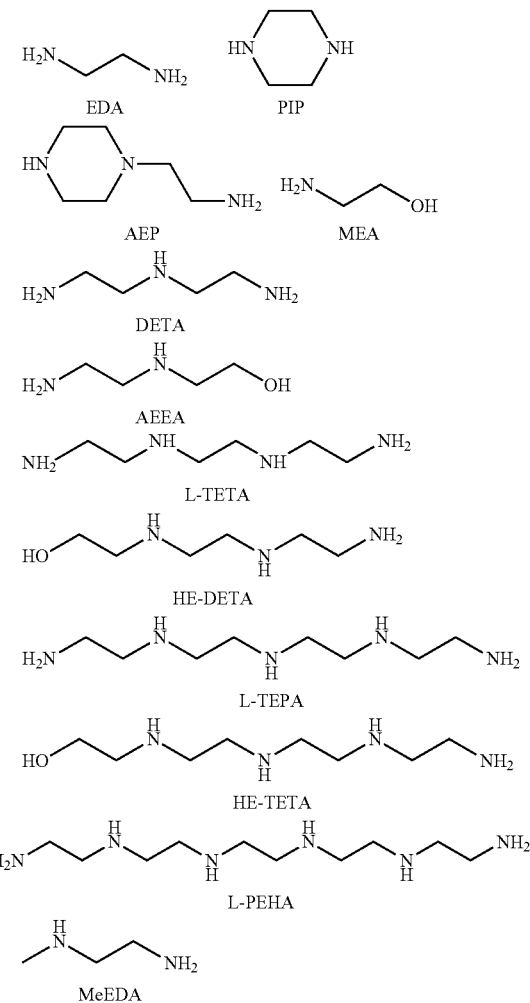

Preferred examples of product polyethylene amine compounds are triethylene tetramine (TETA), N,N'-diaminoethylpiperazine (DAEP), tetraethylenepentamine (TEPA), pentaethylenehexamine (PEHA), N-[(2-aminoethyl) 2-aminoethyl]piperazine) (PEEDA), and 1-[2-[[2-[(2-aminoethyl)amino]ethyl]amino]ethyl]piperazine) (PEDETA).

In one embodiment, aminoethylethanolamine (AEEA) is reacted with ethylenediamine (EDA) to form higher ethylene polyamines, mainly triethylenetetramine (TETA) and tetraethylenepentamine (TEPA).

In another embodiment MEA (monoethanolamine) and DETA (diethylenetriamine) are reacted to form higher ethylene polyamines, mainly triethylenetetramine (TETA) and tetraethylenepentamine (TEPA).

Adduction Step

As indicated above, the adduction step can be an absorption step or a CO2 transfer step, or a combination of these two embodiments. Of course, the CO2 adduct can also be provided as such from other sources. The absorption step and the CO2 transfer step are elucidated below.

Absorption Step

In the absorption step of the process according to the invention, CO2 is absorbed in a reaction medium comprising a starting compound comprising a —NH—CH2-CH2-NH— moiety or a —NH—CH2-CH2-OH moiety, or HO—CH2-CH2-OH to form a CO2 adduct of said starting compound. CO2 adducts of these compounds thus include compounds which a —NH—CH2-CH2-NH— moiety is converted to a urea moiety in which two nitrogen atoms are connected via a carbonyl moiety and an ethylene moiety, in accordance with the following formula:

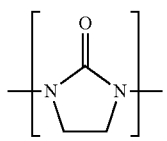

CO2 adducts also include carbamate compounds in which the —NH—CH2-CH2-OH moiety is converted to a carbamate moiety in which the O-atom and the N-atom of the —NH—CH2-CH2-OH moiety are connected through via a carbonyl moiety and an ethylene moiety. CO2 adducts also include compounds in which the HO—CH2-CH2-OH is converted to a ethylenecarbonic acid molecule which the two O-atoms of HO—CH2-CH2-OH are connected through via a carbonyl moiety and an ethylene moiety.

In the above, the CO2 adducts are presented as adducts formed by reaction within a single molecule. Of course, CO2 adducts can also be formed by reaction of reactive groups of different molecules. Within the context of the present specification a CO2 adduct moiety is in many embodiments a moiety wherein two nitrogen atoms, or a nitrogen atom and an oxygen atom, or two oxygen atoms, are connected through a —C(O)— moiety. Furthermore CO2 adducts can also form with a single amine or alcohol in a terminal single sided group, i.e. they can be adducts linked to only one nitrogen or oxygen atom.

The absorption step is carried out by contacting CO2 with a reaction medium comprising a starting compound comprising a —NH—CH2-CH2-NH— moiety or a —NH—CH2-CH2-OH moiety, or HO—CH2-CH2-OH to form a CO2 adduct. The contacting step is to be carried out under such conditions that CO2 is absorbed and that a CO2 adduct is formed.

Reaction conditions include a reaction temperature which generally is at least 120° C. At a temperature below 120° C., the reaction rate generally is too low to allow meaningful conversion within a reasonable time frame. It may be preferred for the reaction temperature to be at least 140° C., in particular at least 150° C., more in particular at least 170° C. The reaction is generally carried out at a temperature of at most 400° C. The temperature may thus be at most 300° C., in particular at most 250° C., or even at most 220° C. Operating at a temperature of 170-220° C. is considered preferred.

The pressure during the reaction is determined for the major part by the provision of CO2 to the reaction medium, with the total pressure in the system decreasing during the reaction due to the consumption of CO2. In general, the total pressure in the system is at most 75 bara. The total pressure generally is at least 2 bara, in particular at least 5 bara, more in particular at least 10 bara.

The amount of CO2 provided to the reaction is not critical. The minimum amount is governed by the amount required to convert the starting material amine compound into its corresponding CO2 adduct. Therefore, the molar ratio between CO2 and —NH—CH2-CH2-NH— moieties, —NH—CH2-CH2-OH moieties, or HO—CH2-CH2-OH generally is at least 0.1:1. A ratio of at least 0.2:1, in particular at least 0.5:1 may be more attractive is more urea adduct is aimed for. A large excess of CO2 is not detrimental to the process, but is generally less attractive for economic reasons. Therefore, as a general maximum a value of 500:1 may be mentioned. The amount of CO2 dosed will depend on the desired amount of urea adduct in the final product.

In one embodiment, the absorption step is carried out by reacting a compound selected from the group of starting amine-functional and hydroxy-functional compounds comprising at least one —NH—CH2-CH2-NH— moiety and at least two ethylene moieties, with CO2 in the presence of an auxiliary compound selected from ethylenediamine (EDA), monoethanolamine (MEA) and mixtures thereof, the molar ratio of auxiliary compound to amine compound being at least 0.02:1. This process is described in non-prepublished European patent application 17172487.5, the disclosure of which is incorporated herein by reference, and the PCT and other applications claiming priority therefrom, which are also incorporated by reference.

For the process of this embodiment it is preferred for the ethyleneamine compound to selected from diethylenetriamine (DETA), triethylenetetramine (L-TETA), aminoethylethanolamine (AEEA), and hydroxyethyldiethylenetriamine (HE-DETA). It is preferred for the molar ratio of auxiliary compound to amine compound to be at least 0.05:1, in particular at least 0.1:1, and/or at most 10:1. It is preferred for the reaction to be carried out at a temperature of at least 120° C., preferably at least 140° C., in particular at least 150° C., more in particular at least 170° C., and/or at most 400° C., in particular at most 350° C., more in particular at most 300° C., still more in particular at most 250° C. or even at most 220° C., for example at a temperature of 170-250° C. or 170-220° C. It is preferred for the molar ratio between CO2 and —NH—CH2-CH2-NH— moieties in the amine compound to be at least 0.5:1 and/or at most 500:1. It is preferred for the reaction time to be at most 10 hours, in particular at most 6 hours, more in particular at most 3 hours and/or at least 5 minutes, in particular between 0.5 and 2 hours.

In one embodiment, the absorption step is carried out via a two-step process wherein
  in an absorption step a liquid medium comprising an ethyleneamine compound having a linear NH—CH2-CH2-NH— group is contacted with a CO2-containing gas stream at a pressure of at most 20 bara, resulting in the formation of a liquid medium into which CO2 has been absorbed,
  bringing the liquid medium to CO2 adduct formation conditions, and in a CO2 adduct formation step forming a CO2 adduct of the ethyleneamine compound, the CO2 adduct formation conditions including a temperature of at least 120° C., wherein the total pressure at the end of the CO2 adduct formation step is at most 20 bara, wherein the temperature in the absorption step is lower than the temperature in the CO2 adduct formation step.

This process is described in non-prepublished European patent application 17185947.3 the disclosure of which is incorporated herein by reference, and the PCT and other applications claiming priority therefrom, which is also incorporated by reference.

By separating the CO2 absorption step from the urea formation step in this embodiment the CO2 absorption step can be carried out at relatively low temperatures and pressures. And because the CO2 is already present in the system at the beginning of the urea formation step. In the absorption step CO2 is absorbed in the liquid reaction medium. In the reaction step the absorbed CO2 is reacted with the ethyleneamine compound to form an cyclic urea adduct. This means that in the urea formation step the provision of further CO2 is not required, and that the absorption step is carried out until sufficient CO2 has been absorbed in the liquid medium to achieve the desired conversion of ethyleneamine compound into cyclic ureas in the urea formation step. As indicated above, the provision of further CO2 to the reaction medium during the urea formation step (in addition to the CO2 provided during the absorption step) is not required, and generally not attractive because it will increase the pressure during the urea formation step. If so desired for some reason, at most 20% of the total CO2 required to achieve the desired urea conversion is added during the urea formation step, in particular at most 10%. In one embodiment of this embodiment, the CO2-containing gas stream comprises at least 95 vol. % of CO2. In another embodiment of this embodiment, the CO2-containing gas stream comprises at most 70 vol. % of CO2, in particular at most 60 vol. % of CO2 and above 0.01 vol. %, in particular between 4 and 60 vol. %. It may be preferred for the step of contacting the liquid medium with the CO2-containing gas steam in the absorption step to be carried out at a temperature between 0° C. and 200° C., in particular at a temperature of at most 190° C., more in particular at most 150° C., or at most 130° C., more in particular at most 110° C. and preferably at a value of at least at least 20° C., in particular at least 40° C. It may be preferred for the maximum total pressure in the absorption step to be between 1 and 15 bara, more in particular between 1 and 10 bara, even more in particular between 1 and 3 bara. It may be preferred for the temperature in the urea formation step to be at least 140° C., in particular at least 150° C., more in particular at least 170° C. and preferably at most 400° C., in particular at most 300° C., more in particular at most 250° C., or even at most 220° C. The urea formation step is preferably carried out in a closed vessel. It may be preferred for the urea formation step to be carried out in a vessel wherein the volume of the liquid medium in the vessel makes up at least 50% of the total volume of the vessel (including head space), in particular at least 70%, more in particular at least 85%. It may be preferred for the pressure at the end of the cyclic urea formation step is below 15 bara, in particular below 10 bara, in some embodiments below 5 bara, or even below 3 bara.

CO2 Transfer Step

In one embodiment the adduction step comprises a CO2 transfer step. In a CO2 transfer step, a carbonyl group is provided from a CO source to a starting compound comprising a —NH—CH2-CH2-NH— moiety or a —NH—CH2-CH2-OH moiety, or HO—CH2-CH2-OH in an adduction step providing a CO2 adduct of a starting compound comprising a —NH—CH2-CH2-NH— moiety or a —NH—CH2-CH2-OH moiety, or HO—CH2-CH2-OH. The CO sources have been discussed above.

Reaction conditions include a reaction temperature which generally is at least 100° C. At a temperature below 100° C., the reaction rate generally is too low to allow meaningful conversion within a reasonable time frame. It may be preferred for the reaction temperature to be at least 125° C., in particular at least 150° C., more in particular at least 170° C. The reaction is generally carried out at a temperature of at most 400° C. The temperature may thus be at most 300° C., in particular at most 250° C., or even at most 220° C. Operating at a temperature of 170-220° C. is considered preferred.

In general, the total pressure in the system is at most 75 bara. The total pressure generally is at least 2 bara, in particular at least 5 bara, more in particular at least 10 bara. The amount of CO moieties provided to the reaction is not critical. The minimum amount is governed by the amount required to convert the starting material amine compound into its corresponding CO2 adduct. Therefore, the molar ratio between CO moieties and independent —NH—CH2-CH2-NH— moieties, —NH—CH2-CH2-OH moieties, or HO—CH2-CH2-OH generally is at least 0.1:1. A ratio of at least 0.2:1, in particular at least 0.5:1 may be more attractive is more urea adduct is aimed for. A large excess of CO moieties is not detrimental to the process, but is generally less attractive for economic reasons. Therefore, as a general maximum a value of 500:1 may be mentioned. The amount of CO moieties dosed will depend on the desired amount of urea adduct in the final product.

Reaction Step

In the reaction step of the process according to the invention a hydroxy-functional compound selected from the group of ethanolamines and dihydroxyethane is reacted with an amine-functional compound, wherein at least part of the total of hydroxy-functional compounds and amine-functional compounds is provided in the form of a CO2 adduct, to form a CO2 adduct of a polyethyleneamine compound.

The process is preferably performed at a temperature of at least 100° C. The temperature should preferably be lower than 400° C. More preferably the temperature is between 200 and 360° C. Even more preferably the temperature is between 230 and 340° C. Most preferably the temperature is between 250 and 310° C. In embodiments where the ethanolamine-functional compound is monoethanolamine the most preferred temperature range is between 230 and 290° C.

The reaction time during the process is in an embodiment between 5 minutes and 15 hours, preferably between 0.5 and 10 hours, more preferably between 1 and 6 hours.

It will be clear to the skilled person that an overly long reaction time will be detrimental, not only for process-economical reasons, but also because it may lead to the formation of undesirable high-boiling side products. In extreme cases a too long reaction time can lead to undesirable degradation and color formation.

If any of the starting compounds contains piperazine units

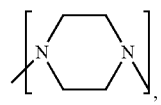

preferably the reaction is performed in a liquid wherein the liquid comprises water as then both the yield and selectivity can be increased. If one or more of the hydroxy-functional compound, amine-functional compound or carbon oxide delivering agent are liquid at the reaction conditions, these are not considered part of the above liquid in which the process of the invention is performed.

In a preferred embodiment when having compounds with piperazine units in the process of the invention, the liquid contains at least 50 wt % of water up to 100 wt % of water, wherein more preferably the remaining up to 50 wt % is a polar liquid that mixes homogenously with water at the conditions employed during the process of the invention. Even more preferably the liquid contains at least 75 wt-% of water, yet more preferably at least 90 wt-%, most preferably at least 95-wt % on total liquid weight.

The reactor employed can be any suitable reactor including continuously stirred tank reactor, pipeline reactor, tubular or multi-tubular reactor. The reactor may be adiabatic or equipped with external or internal heating devices. Feed may be single point or split into multiple points. It can consist of multiple stages with inter-stage heat exchange.

As will be clear to the skilled person, the apparatus used in the reaction step, but also in the various other steps of the process according to the invention, should be fit for purpose. That is, they should be able to withstand the long-time interaction with the reactants and products under reaction conditions, including, as described elsewhere, substantial temperatures and pressures. In addition to the reactor and other apparatus being able to withstand the reaction conditions, it is also important that they do no release material which would detrimentally affect the quality of the product produced. For example, as metal ions may result in color formation in the product, the material of construction for the various apparatus should be selected such that metal ions are not released to an unacceptable extent. Suitable materials include, but are not limited to, high quality steels such as austenitic stainless steels, super austenitic stainless steels, ferritic stainless steels, martensitic stainless steels, precipitation-hardening martensitic stainless steels, and Duplex stainless steels. It is within the scope of the skilled person to select suitable materials of construction.

The process can be carried out in one or multiple batch reactors, possibly in fed-batch operation, and/or in a continuously operating system in one reactor or in a cascade of continuous flow reactors, optionally with multiple feeding points.

It was found that when adding at least 0.6 molar equivalents of carbon oxide delivering agent on amine-functional compound, the yield of ethyleneamines increases considerably and also the amount of side products decreases.

Hence it is preferred to have the molar ratio of $CO_2$ and/or carbon oxide delivering agent to amine-functional compound at least 0.6 to 1.

Preferably, the molar amount of $CO_2$ and/or carbon oxide delivering agents on amine-functional compounds is between 0.7 and 20 molar equivalents of carbon oxide delivering agent on moles of amine functional compound, and more preferably it is between 0.7 and 6:1, even more preferably between 0.8:1 and 3:1.

In another embodiment that leads to a high yield, the molar ratio of hydroxy-functional compound to amine-functional compound is at least 0.7:1 and the molar ratio of carbon oxide delivering agent to amine-functional compound is at least 0.05:1. In such embodiments the yield of ethylene amines is also high.

Even more preferably the molar ratio of hydroxy-functional compound to amine-functional compound is between 0.8 and 5:1 and the molar ratio of carbon oxide delivering agent to amine functional compound is between 0.2:1 and 20:1.

Yet even more preferably the molar ratio of hydroxy-functional compound to amine-functional compound is between 1:1 and 2:1 and the molar ratio of carbon oxide delivering agent to amine-functional compound is between 0.7:1 and 3:1

To achieve a high selectivity of ethylene amine on starting materials, especially on hydroxy-functional compound, the molar ratio of hydroxy-functional compound to amine-functional compound is preferably between 0.05:1 and 0.7:1 and the molar ratio of $CO_2$ and/or carbon oxide delivering agent to amine-functional compound is higher than the molar ratio of hydroxy-functional compound to amine-functional compound More preferably the molar ratio of $CO_2$ and/or carbon oxide delivering agent to amine-functional compound is at least 10% higher than the molar ratio of hydroxy-functional compound to amine-functional compound. In another more preferred embodiment the molar ratio of hydroxy-functional compound to amine-functional compound is between 0.1 and 0.5.

It should be noted that carbon oxide delivering agents exist that contain more than one carbonyl group that can be released from the molecule for transfer to the hydroxy-functional compound, such as for example DU-TETA. When determining the molar ratio for such compounds there should be an adjustment for the molar amount of carbon oxide they can release for transfer to the hydroxyl-functional compound. Accordingly, 1 mole of DU-TETA should be considered 2 moles of carbon oxide delivering agent.

The molar ratio, as above, between compounds is determined by the reactants in the process, independent of the dosing regime used for the reactants.

In some embodiments it is favorable to at least partially combine the reaction step with the separation, and/or elimination step by performing a reactive separation step, such as a reactive distillation. In a reactive separation step the above reaction step finds place under conditions selected such that the $CO_2$ adduct of the starting compounds reacts to give $CO_2$ adduct of product polyethyleneamine and in the same reactive separation the formed $CO_2$ adduct of product polyethyleneamine is either separated from other components, or transfers it CO moiety to another component in the reactor, which can be either remaining starting compounds or byproducts. This step is also indicated as a $CO_2$ transfer step. This process is described in non-prepublished European patent application 17185943.2, the disclosure of which is incorporated herein by reference and the PCT and other applications claiming priority therefrom, which are also incorporated by reference.

In one embodiment cyclic alkylene ureas are converted into their corresponding alkylene amines by reaction with an amine compound chosen from the group of primary amines or secondary amines that have a higher boiling point than the alkylene amines formed during the process, wherein the process is a reactive separation process and the reaction mixture contains less than 10 wt % of water on the basis of total weight of the reaction mixture. It may be preferred to carry out the reaction in less than 7 wt % of water on total reaction mixture. It may be preferred for the pressure to be less than 25 bara, in particular less than 500 mbara. In general, the reaction will be done at a temperature of at least 150° C.

Elimination Step

As indicated above, the elimination step can comprise a desorption step, a CO transfer step, a treatment with (strong) inorganic base, or a combination of one or more of the above. The steps will be elucidated below.

In the elimination step, $CO_2$ adducts of polyethyleneamine compounds are converted to $CO_2$ and polyethyleneamine compounds. It is preferred for at least 10 mole % of the $CO_2$ adduct moieties in the system to be converted to the corresponding ethyleneamine moieties. The maximum will depend on the following desorption and recycle steps.

Desorption Step

In the desorption step, $CO_2$ adducts of ethyleneamine compounds are converted into ethyleneamine compounds by reaction with water, with removal of $CO_2$. The reaction takes place in the liquid phase.

The reaction with water generally takes place at a temperature of at least 150° C. If the reaction temperature is below 150° C., $CO_2$ adducts of ethyleneamine compounds will not react to a significant extent. It is preferred for the reaction to be carried out at a temperature of at least 180° C., in particular at least 200° C., more in particular at least 230° C., or even at least 250° C. Preferably the temperature during this step does not exceed 400° C., in particular at most 350° C., more in particular at most 320° C.

The pressure during the process is not critical, as long as the reaction medium is in the liquid phase. As a general range, a value of 0.5 to 100 bara may be mentioned, depending on the desired temperature. It is preferred for the $CO_2$ removal step to be carried out at a pressure of at least 5 bar, in particular at least 10 bar, to maintain a sufficient amount of amine and water in the medium. In view of the high costs associated with high-pressure apparatus, it may be preferred for the pressure to be at most 50 bar, in particular at most 40 bar.

The amount of water depends on the desired degree of conversion and on the process conditions. In general, the amount of water is at least 0.1 mole water per mole $CO_2$ adduct moiety in the feedstock. Higher amounts are often used, e.g., at least 0.2 mole per mole $CO_2$ adduct moiety, in particular at least 0.5 mole water per mole $CO_2$ adduct moiety. The maximum is not critical for the process according to the invention but too large amounts of water will lead to unnecessarily large equipment being required. As a general maximum an amount of at most 500 mole water per mole cyclic ethylene $CO_2$ adduct moiety may be mentioned, in particular at most 300 mole, more in particular at most 200 mole, in some embodiments at most 100 mole, or at most 50 mole.

Depending on the reaction temperature and the desired degree of conversion, the reaction time can vary within wide ranges, e.g., at least one minute, in particular at least 5 minutes, more in particular between 15 minutes and 24 hours. In one embodiment, the reaction time may be at least 30 minutes, or at least 1 hour. It may be preferred for the reaction time to vary between 1 hour and 12 hours, in particular between 1 hour and 6 hours. When using lower temperatures, longer reaction times may be required to obtain the desired degree of conversion.

In one embodiment of the present invention, the desorption step is carried out by reacting $CO_2$ adducts of ethyleneamine compounds in the liquid phase with water in an amount of 0.1-20 mole water per mole $CO_2$ adduct moiety, at a temperature of at least 230° C., with removal of $CO_2$. It has been found that the use of a low amount of water in combination with a relatively high temperature and $CO_2$ removal results in an efficient process which good conversion and low formation of side products. It has been found that it is possible in this embodiment of the process according to the invention to obtain good conversion with the relatively limited amount of water of at most 20 mole water per mole $CO_2$ adduct moiety. It has been found that it possible to work at even lower amounts of water, e.g., and amount of at most 15 mole water per mole $CO_2$ adduct moiety, more in particular an amount of at most 10 mole water per mole $CO_2$ adduct moiety, or even at most 5 mole water per mole $CO_2$ adduct moiety.

The range of 0.1-20 mole water per mole $CO_2$ adduct moiety refers to the entire amount of water added during the process, calculated on the amount of urea moieties in feedstock at the start of the reaction. To obtain full conversion, 1 mole of water is required per mole $CO_2$ adduct moiety to be converted. As full conversion is not always necessary, lower amounts of water may be possible. Therefore, water is used in an amount of at least 0.1 mole per mole $CO_2$ adduct moiety. Higher amounts are often used, e.g., at least 0.2 mole per mole $CO_2$ adduct moiety, in particular at least 0.5 mole water per mole $CO_2$ adduct moiety.

Water can be added at the beginning of the desorption step in a single dosing. It is preferred, however, to add the water during the process, in several dosings or continuously. In a continuous operation multiple feedpoints may be used. By matching the amount of water added to the amount of water consumed by the reaction, the excess water in the reaction mixture can be limited. It has been found that this limits the formation of side products.

The molar ratio of water to urea moieties is calculated on the water present in the liquid reaction medium. If water is added in the form of steam, which may be an attractive embodiment to combine water addition with the provision of heat to the reaction mixture, the majority of water in the steam will not be absorbed in the liquid reaction medium. It is within the scope of the skilled person to regulate the conditions of a water addition process via stream in such a way that the desired amount of water is absorbed by the reaction medium. The water can also be present in the feedstock from the beginning of the reaction, e.g., as a result of the process by which the feedstock was produced. Water can also be added as a liquid.

In one embodiment of the desorption step, $CO_2$ is removed. $CO_2$ removal can be carried out when the conversion of the alkyleneureas into ethyleneamine compounds has been completed. However, it is preferred to carry out $CO_2$ removal during the reaction. $CO_2$ removal can be carried out in manners known in the art. The most basic way to do this it to vent the reaction vessel. A stripping fluid, in particular a stripping gas can be used to increase $CO_2$ removal rate. Other measures to improve removal of $CO_2$ will be evident to the skilled person, and include measures like stirring of the reaction mixture, sparging of stripping gas, thin-film evaporation, use of packing or trays, etc.

Where a stripping gas is used, the flow rate is typically at least 1 m3 per 1 m3 reactor volume per hour (at reaction temperature and pressure), and at most 100 m3 per 1 m3 reactor volume per hour (at reaction temperature and pressure). The stripping flow rate can be generated by evaporation of a liquid inside the reactor vessel, resulting in in situ generation of stripping gas. The ranges above also apply to this embodiment. Of course, it is also possible to combine the addition of tripping gas with the in situ formation of stripping gas.

The $CO_2$-containing stripping fluid removed from the $CO_2$ removal step can, for example, comprise from 1 to 99 mol. % $CO_2$. In other embodiments, the stripping fluid may comprise 1-80 mol. % $CO_2$, or 1-60 mol. % $CO_2$. In some embodiments, the effluent from the $CO_2$ removal step may comprise 1-40 mol. % $CO_2$, or 1-20 mol. % $CO_2$. Lower $CO_2$ contents make for more efficient stripping, but also for the use of more stripping gas. It is within the scope of the skilled person to find an appropriate balance between these parameters.

If so desired the desorption step can be carried out with water in the presence of an amine compound selected from the group of primary amines, cyclic secondary amines, and bicyclic tertiary amines. This embodiment is a variation on the process described in earlier filed non-prepublished PCT application No. PCT/EP2017/052944, which is incorporated herein by reference also for priority purposes.

Primary amines are amine functional compounds in which the amine group is of the formula R4-NH2 and wherein R4 can be any organic group, preferably an aliphatic hydrocarbon with optional heteroatoms such as oxygen and/or nitrogen. Secondary cyclic amines are amines of the formula R5-NH—R6, wherein R5 and R6 together form a hydrocarbon ring, optionally with heteroatoms such as oxygen and/or nitrogen, preferably a piperazine ring. Tertiary bicyclic amines are amines of the formula R7-N(—R9)-R8 where R7 and R8 together form a hydrocarbon ring—optionally with heteroatoms such as oxygen and/or nitrogen—and R7 and R9 together form another hydrocarbon ring—optionally with heteroatoms such as oxygen and/or nitrogen. On all the above groups R4 to R9 substituents can be present, like alkyl or hydroxyalkyl groups. Primary amines, cyclic secondary amine and bicyclic tertiary amines all contain a sterically relatively unhindered amine group. In this document a compound is defined as a primary amine or a secondary cyclic amine or a tertiary bicyclic amine if one of the amine groups in the compound is a primary amine or secondary cyclic amine or a tertiary bicyclic amine group, independent of if this compound contains further amine groups that may be different in their nature. A compound can also contain two or more different amine functionalities, e.g. a primary amine and a secondary cyclic amine functionality or a primary amine, a secondary cyclic amine and a tertiary bicyclic amine functionality.

Preferred examples of primary amines are alkylamines, linear ethylene amines, and alkanolamines. Preferred examples of cyclic secondary amines are amines that contain a terminal piperazine ring. Preferred examples of bicylic tertiary amines are 1,4-diazabicyclo[2.2.2]octane (DABCO), 1,4-diazabicyclo[2.2.2]octan-2-yl)methanol and 1-azabicyclo[2.2.2]octane (Quinuclidine).

The amine compound is preferably a compound with more than one amine group wherein at least one of the amine groups is a primary amine, even more preferably it is an amine wherein two amine groups are a primary amine.

Preferred amine compounds include ethylenediamine (EDA), N-methylethylenediamine (MeEDA), diethylenetriamine (DETA), ethanolamine (MEA), aminoethylethanolamine (AEEA), piperazine (PIP), N-aminoethylpiperazine (AEP), 1,4-diazabicyclo[2.2.2]octane (DABCO), 1,4-diazabicyclo[2.2.2]octan-2-yl)methanol, triethylenetetramine (TETA), N-diethyldiamine-2-imidazolidinone (U1TETA), N,N'-diaminoethylpiperazine (DAEP), N,N'-diaminoethyl-2-imidazolidinone (U2TETA), tetraethylenepentamine (TEPA), pentaethylenehexamine (PEHA), and the mono cyclic ureas of TEPA and PEHA (i.e. U1TEPA, U2TEPA, U1PEHA, U2PEHA, U3PEHA) and the dicyclic urea isomers of PEHA (i.e. DUPEHA), a polyethyleneimine (PEI) or an alkylene amine on a solid carrier.

The amine compound is preferably present in a molar amount of between 0.001 and 100 equivalents per mole CO2 adduct moiety, more preferably between 0.01 and 50 equivalents, even more preferably between 0.05 and 30 equivalents, yet more preferably between 0.15 and 25 equivalent and most preferably between 0.20 and 20 equivalents.

In the desorption step, CO2 adducts of ethyleneamine compounds are converted to CO2 and ethyleneamine compounds. It is preferred for at least 10 mole % of the CO2 adduct moieties in the system to be converted to the corresponding ethyleneamine moieties. The maximum will depend on the following desorption and recycle steps.

Treatment with (Strong) Inorganic Base

In one embodiment, an elimination step is carried out using a (strong) inorganic base. Within the context of the present invention, a strong inorganic base is a base with a material which does not contain carbon-carbon bonds and which has a pKb of less than 1.

In one embodiment, the strong inorganic base is selected from the group of metal hydroxides, in particular from the group of hydroxides of alkaline and earth alkaline metals, in particular from sodium hydroxide, potassium hydroxide, lithium hydroxide, calcium hydroxide, magnesium hydroxide, and barium hydroxide. In one embodiment, the strong inorganic base is selected from the group of metal oxides, in particular from the group of oxides of alkaline and earth alkaline metals, in particular from calcium oxide, magnesium oxide, and barium oxide. Selecting a strong inorganic base from the group of sodium hydroxide, potassium hydroxide, magnesium (hydr)oxide, and calcium (hydr)oxide may be preferred. The use of sodium hydroxide and potassium hydroxide may be particularly considered preferred. Other strong inorganic bases may also be used, such as ammonium hydroxide. As will be evident to the skilled person, mixtures of various inorganic bases can be used. Compounds comprising a base in addition to other components can also be used, as can be compounds which will be converted into inorganic bases in the reaction medium.

The lower limit of the molar ratio of inorganic base to CO2 adduct moieties is not critical. A value of at least 0.2:1 may be mentioned. If it is desired to obtain full conversion of the CO2 adduct moieties into the corresponding ethyleneamine compound, the use of larger amounts may be preferred, e.g., in a molar ratio of at least 0.5:1, in particular at least 1:1. It may be preferred to use larger amounts to increase the reaction rate, e.g., a molar ratio of inorganic base to CO2 adduct moiety of at least 1.5:1, in particular at least 2:1.

As large amounts of base do not contribute to further conversion but will lead to additional costs, it is preferred for the molar ratio of the inorganic base to the molar amount of CO2 adduct moieties in the product provided to the treatment with the inorganic base to be at most 20:1, in particular at most 15:1, more in particular at most 10:1. It has been found that even lower amounts of inorganic base can suffice, in contrast to what has been disclosed in the prior art. More in particular, it has been found that good results can be obtained at a molar ratio of inorganic base to CO2 adduct moieties of at most 7.5:1, in particular at most 6.5:1, even more in particular at most 5.5:1. It has been found that the use of a molar ratio of at most 5.5:1 results in full conversion of the CO2 adduct moieties and high yield of the resulting ethyleneamine compounds. It may be preferred to use even less inorganic base per mole of CO2 adduct moiety, e.g., in a more ratio of at most 5:1, in particular at most 4:1, more in particular at most 3:1. The molar ratio is calculated on the molar amount of CO2 adduct moieties in the feed provided to the caustic treatment step.

The treatment with inorganic base can, for example, be carried out by contacting the material to be treated with a concentrated aqueous solution of the inorganic base. Depending on the nature of the base and the further composition of the reaction mixture, it may also be possible to add the base in solid form and dissolve it in the reaction medium. As will be clear to the skilled person, the aim is to bring the base in a dissolved state, so that the hydroxy groups can react with the CO2 adduct, while avoiding unnecessary dilution of the reaction medium.

The reaction can be carried out at a temperature between room temperature and 400° C. The temperature and pressure should be selected such that the reaction mixture is in the liquid phase. Higher temperatures are advantageous because they lead to decreased reaction times. It may be preferred to carry out the reaction at a temperature of at least 100° C., in particular at least 140° C., in particular at least 170° C. On the other hand, higher temperatures may lead to the undesired formation of side products. It may therefore be preferred to carry out the reaction at a temperature of at most 350° C., in particular at most 280° C.

Depending on the reaction temperature, the reaction time can vary within wide ranges, e.g., between 15 minutes and 24 hours. It may be preferred for the reaction time to vary between 1 hour and 12 hours, in particular between 1 hour and 6 hours. When using lower amounts of base, longer reaction times may be required to obtain the desired degree of conversion.

Upon completion of the reaction, a reaction mixture will be obtained which contains ethyleneamine compounds and a carbonate salt of the inorganic base. The salt can be removed by methods known in the art, e.g., by filtration where the salt is in solid form.

The process according to the invention can be carried out in batch operation, fed-batch operation, or in a continuous operation, e.g., in a cascade of continuous flow reactor. Depending on the scale of the operation, continuous operation may be preferred.

Combination of Elimination Steps

A particular combination of elimination steps include a desorption step followed by a treatment with strong inorganic base, optionally after a separation step in which desired compounds have been removed. Reference is made to non-prepublished European patent application 17185950.7, the disclosure of which is incorporated herein by reference, and the PCT and other applications claiming priority therefrom, which are also incorporated by reference.

In one embodiment, this combination encompasses the conversion of cyclic alkyleneureas into their corresponding alkyleneamines by a process comprising in a first step converting cyclic alkyleneureas into their corresponding alkyleneamines by reacting cyclic alkyleneureas in the liquid phase with water with removal of CO2, so as to convert between 5 mole % and 95 mole % of alkyleneurea moieties in the feedstock to the corresponding amines, and in a second step adding a inorganic base and reacting cyclic alkylene ureas remaining from the first step with the inorganic base to convert them completely or partially into their corresponding alkyleneamines.

Another particular combination of elimination steps include a combination of one or more desorption steps with one or more reactive separation steps. The reactive separation encompasses CO2 transfer wherein the carbonyl group from the CO2 adduct of the product polyethyleneamine compound is transferred to a compound having a —NH—CH2-CH2-NH— moiety or a NH—CH2-CH2-OH moiety, or HO—CH2-CH2-OH. Reference is made to non-prepublished European patent application 17185945.7, the disclosure of which is incorporated herein by reference.

In one embodiment this combination encompasses the conversion of a feedstock comprising cyclic alkyleneureas into their corresponding alkyleneamines, by a process comprising a desorption step in which cyclic alkyleneureas are converted into their corresponding alkyleneamines by reacting cyclic alkyleneureas in the liquid phase with water with removal of CO2, a reactive separation step wherein cyclic alkyleneureas are converted into their corresponding alkyleneamines by reaction with an amine compound selected from the group of primary amines or secondary amines which have a higher boiling point than the alkyleneamines formed during the process.

The reactive separation step may preferably be carried out as a reactive distillation step. This embodiment is also discussed above in the context of the reaction step.

In one embodiment the desorption step precedes the reactive separation step. In another embodiment, the reactive separation step precedes the desorption step. It is also possible to perform at least two desorption steps, with one or more reactive separation step being performed in between, or at least two reactive separation steps, with one or more reactive desoption steps being performed inbetween.

The reactive separation step may be conducted at any suitable pressure. During the reaction, the pressure in the reactive separation system preferably is at most 127 bara, more preferably at most 50 bara, and even more preferably at most 25 bara. Depending on the composition of the reaction medium, lower pressures may be applied, e.g., less than 15 bar, or less than 5 bar. The process can also be carried out at a pressure below atmospheric pressure, such as less than 700 mbara, more preferably below 100 mbara, even more preferably below 25 mbara, and most preferably below 5 mbara. In general the pressure will be at least 0.1 mbara.

The reactive separation step is preferably carried out at a temperature of at least 150° C., in particular at least 180° C., in some embodiments at least 200° C., or at least 230° C., sometimes at least 250° C. Preferably the temperature during the process does not exceed 400° C., more preferably 350° C. In one embodiment, the reactive separation step amine removal step is carried out at a temperature in the range of 180–300° C. and a pressure of at most 2000 mbara, in particular at most 1000 mbara, more in particular at most 500 mbara, more in particular at most 200 mbara. It may be preferred to carry out the reactive separation step at a temperature of 200-260° C. and a pressure of at most 50 mbara. The reactive separation step generally is performed for a time of between 1 minute and 12 hours. Preferably the reactive separation step is run in less than 10 hours, more preferably in less than 8 hours, most preferably less than 5 hours.

Separation Step

At various points in the process according to the invention, separation steps may be carried out. They can be carried out by methods known in the art, as will be evident to the skilled person.

For example, as indicated above, the product from the reaction step can be subjected to a separation step to separate starting compounds from (CO2 adducts of) product polyethyleneamine compound. This separation step can be carried out, e.g., through distillation as the starting compounds have a lower boiling point than the product polyethyleneamine compounds or CO2 adducts thereof.

The desorption step is accompanied by the production of CO2, which is removed from the reaction mixture, after or during the desorption step. This is thus also a separation step. It will be clear to the skilled person how this step can be carried out. Reference is also made to what has been stated above.

In various locations in the process according to the invention, further separation steps may be carried out, in which product polyethyleneamine compounds are separated from starting compounds, intermediate compounds and/or from CO2 adducts of product polyethyleneamine compounds. Again, this process can suitably be carried out by a distillation process. Other suitable methods will be evident to the skilled person.

As will be evident to the skilled person, it is possible in the process according to the invention where there are multiple steps, to combine the products of different runs of the same step, and subject the combined product to the further steps. If so desired, product generated by other processes can also be included. Conversely, it is also possible to split product fractions from one step and provide them to different units.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. An integrated process for manufacturing polyethyleneamine compounds selected from the group of polyethyleneamines and hydroxyethylethyleneamines comprising the steps of:
   in an adduction step, providing a $CO_2$ adduct of a starting compound comprising a —NH—$CH_2$—$CH_2$—NH— moiety or a NH—$CH_2$—$CH_2$—OH moiety, or HO—$CH_2$—$CH_2$—OH,
   in a reaction step, reacting a hydroxy-functional compound selected from the group of ethanolamines and dihydroxyethane with an amine-functional compound, wherein at least part of the total of hydroxy-functional compounds and amine-functional compounds is provided in the form of a $CO_2$ adduct, to form $CO_2$ adduct of a product polyethyleneamine compound,
   in an elimination step, converting the $CO_2$ adduct of product polyethyleneamine compound to a corresponding product polyethylene amine compound,
   wherein a fraction comprising a recycle compound comprising a NH—$CH_2$—$CH_2$—NH— moiety or a —NH—$CH_2$—$CH_2$—OH moiety, or HO—$CH_2$—$CH_2$—OH, or $CO_2$ adducts thereof, is provided from the end of the reaction step or the elimination step to the adduction step or to the reaction step,
   wherein the recycle compound has per molecule on average fewer of the total of —NH—$CH_2$—$CH_2$—NH— moieties and —NH—$CH_2$—$CH_2$—OH moieties than the product polyethyleneamine compound.

2. The integrated process according to claim 1, wherein the adduction step comprises an absorption step wherein gaseous $CO_2$ is reacted with a starting compound comprising a —NH—$CH_2$—$CH_2$—NH— moiety or a —NH—$CH_2$—$CH_2$—OH moiety, or HO—$CH_2$—$CH_2$—OH, to form a $CO_2$ adduct thereof.

3. The integrated process of claim 1, wherein the adduction step comprises the step of reacting starting compound comprising —NH—$CH_2$—$CH_2$—NH— moiety or a —NH—$CH_2$—$CH_2$-0H moiety, or HO—$CH_2$—$CH_2$—OH with a carbon oxide delivering agent which can transfer a carbonyl group to the starting compounds, resulting in the formation of $CO_2$ adducts thereof.

4. The integrated process of claim 1, wherein the elimination step comprises a desorption step in which the $CO_2$ adduct of product polyethyleneamine compound is reacted with water to form $CO_2$ and the corresponding product polyethylene amine compound.

5. The integrated process of claim 1, wherein the elimination step comprises a caustic treatment step in which $CO_2$ adduct of product polyethyleneamine compound is reacted with an inorganic base, resulting in the formation of a product polyethyleneamine compound and a carbonate salt.

6. The integrated process of claim 1, wherein the elimination step comprises a $CO_2$ transfer step, wherein the carbonyl group from the $CO_2$ adduct of the product polyethyleneamine compound is transferred to a compound having a —NH—$CH_2$—$CH_2$—NH— moiety or a NH—$CH_2$—$CH_2$—OH moiety, or HO—$CH_2$—$CH_2$—OH.

7. The integrated process of claim 1, wherein the adduction step comprises an absorption step and the elimination step comprises a desorption step, and wherein $CO_2$ formed in the desorption step is provided at least in part to the absorption step.

8. The integrated process of claim 1, wherein the adduction step comprises an absorption step and the elimination step comprises a desorption step, and wherein stripping gas withdrawn from the desorption step is subjected to a $CO_2$ removal step and recycled at least in part to the desorption step.

9. The integrated process according to claim 8, wherein stripping gas containing $CO_2$ is removed from the desorption step and provided to absorption step, where $CO_2$ is absorbed from the $CO_2$-containing stripping gas, and stripping gas from which $CO_2$ has been removed is withdrawn from the absorption step and provided to the desorption step.

10. The integrated process of claim 1, wherein a separation step is provided after the elimination step, the separation step yielding a fraction comprising a recycle compound comprising a —NH—$CH_2$—$CH_2$—NH— moiety or a —NH—$CH_2$—$CH_2$—OH moiety, or HO—$CH_2$—$CH_2$—OH, or $CO_2$ adducts thereof, which fraction is provided in its entirety or in part to the adduction step or to the reaction step,
   wherein the recycle compound has per molecule on average fewer of the total of —NH—$CH_2$—$CH_2$—NH— moieties and —NH—$CH_2$—$CH_2$—OH moieties than the product polyethyleneamine compound, the recycle compound comprising starting compounds and optionally intermediate compounds, the separation step further yielding a product fraction of product polyethyleneamine compounds.

11. The integrated process of claim 1, wherein a separation step is provided after the reaction step and before the elimination step, the separation step yielding a fraction comprising a recycle compound comprising a —NH—$CH_2$—$CH_2$—NH— moiety or a —NH—$CH_2$—$CH_2$—OH moiety, or HO—$CH_2$—$CH_2$—OH, or $CO_2$ adducts thereof, which fraction is provided in its entirety or in part to the adduction step or to the reaction step, the separation step further yielding a fraction comprising $CO_2$ adduct of product polyethyleneamine compounds, which fraction is provided to the elimination step.

12. The integrated process of claim 1, wherein the elimination step comprises a first elimination step and one or more further elimination steps, wherein the elimination steps are independently selected from the group consisting of:
a desorption step in which the $CO_2$ adduct of product polyethyleneamine compound is reacted with water to form $CO_2$ and the corresponding product polyethylene amine compound,
a caustic treatment step in which $CO_2$ adduct of product polyethyleneamine compound is reacted with an inorganic base, resulting in the formation of a product polyethyleneamine compound and a carbonate salt, and
a $CO_2$ transfer step, wherein the carbonyl group from the $CO_2$ adduct of the product polyethyleneamine compound is transferred to a compound having a —NH—$CH_2$—$CH_2$—NH— moiety or a NH—$CH_2$—$CH_2$—OH moiety, or HO—$CH_2$—$CH_2$—OH,
wherein the first elimination step converts part of the $CO_2$ adducts of polyethyleneamines present in the feed thereto into the polyethyleneamine compounds, while part of the $CO_2$ adducts of polyethyleneamines present in the feed to the first elimination step is not converted in the first elimination step, and is provided to a further elimination step.

13. The integrated process according to claim 12, wherein the first elimination step is a desorption step or a $CO_2$ transfer step and the further elimination step is a desorption step or a caustic treatment step, wherein the steps are not the same.

14. The integrated process of claim 1, wherein elimination step yields a product comprising polyethyleneamine compounds and $CO_2$ adducts of polyethyleneamine compounds, and this product is provided to a separation step where a fraction comprising $CO_2$ adducts of polyethyleneamine compounds is separated from the polyethyleneamine compounds, and processed in one or more of the following manners:
it is subjected at least in part to purification and further separation steps,
it is recycled at least in part to the elimination step,
it is provided at least in part to a further elimination step which is carried out under more stringent conditions than the first elimination step, and comprises, e.g., a treatment with an inorganic base,
it is provided at least in part to the reaction step.

15. The integrated process of claim 1, wherein the starting materials are provided to the reaction step via one of the following methods:
the amine-compound is provided in its entirety or in part to the adduction step where it is converted into its $CO_2$ adduct, which is then provided to the reaction step, with the hydroxy-functional compound being provided to the reaction step,
the hydroxy-functional compound is provided in its entirety or in part to the adduction step where it is converted into its $CO_2$ adduct, which is then provided to the reaction step, with the amine-functional compound being provided to the reaction step,
the hydroxy-functional compound and the amine-functional compound are both provided to the adduction where they are converted in their entirety or in part to their $CO_2$ adducts, which are provided to the reaction step.

16. The integrated process of claim 1, wherein the adduction step comprises an absorption step and the elimination step comprises a desorption step, and wherein a stream comprising $CO_2$ is withdrawn from the desorption step and provided to the absorption step and a stream comprising water is withdrawn from the absorption step and provided to the desorption step.

17. The integrated process of claim 1, wherein a stream comprising water is withdrawn from the reaction step and provided to the elimination step.

18. The integrated process of claim 1, wherein a separation step is provided after the reaction step and before the elimination step and a further separation step is provided after the elimination step.

19. The integrated process of claim 1, comprising the steps of
providing a starting compound comprising a —NH—$CH_2$—$CH_2$—NH— moiety or a —NH—$CH_2$—$CH_2$—OH moiety, or HO—$CH_2$—$CH_2$—OH to an absorption step where it is combined with $CO_2$ and reacted to form a $CO_2$ adduct,
providing the $CO_2$ adduct to a reaction step where it is reacted with a further reactant, the reactants in the reaction step being a hydroxy-functional compound selected from the group of ethanolamines and dihydroxyethane and an amine-functional compound, wherein at least part of the total of hydroxy-functional compounds and amine-functional compounds is provided in the form of a $CO_2$ adduct, to form a product comprising a $CO_2$ adduct of a polyethyleneamine compound,
providing the product comprising a $CO_2$ adduct of a polyethyleneamine compound to a desorption step, where it is contacted with a stripping gas, and withdrawing a $CO_2$-containing stripping gas from the desorption step and providing it to the absorption step,
withdrawing a stripping gas from which $CO_2$ has been absorbed from the absorption step and providing it to the desorption step,
providing the product from the desorption step to a separation step, which yields a starting material fraction which is provided to the absorption step or to the reaction step, the separation step further yielding a product fraction of polyethyleneamine compounds which is withdrawn for the separation step, and a fraction comprising $CO_2$ adducts of polyethyleneamine compounds, which is provided to the desorption step or to the reaction step.

20. The integrated process of claim 1, comprising the steps of
providing a starting compound comprising a —NH—$CH_2$—$CH_2$—NH— moiety or a —NH—$CH_2$—$CH_2$—OH moiety, or HO—$CH_2$—$CH_2$—OH to an absorption step where it is combined with $CO_2$ and reacted to form a $CO_2$ adduct,
providing the $CO_2$ adduct to a reaction step where it is reacted with a further reactant, the reactants in the reaction step being a hydroxy-functional compound selected from the group of ethanolamines and dihydroxyethane and an amine-functional compound, wherein at least part of the total of hydroxy-functional compounds and amine-functional compounds is provided in the form of a $CO_2$ adduct, to form a product comprising a $CO_2$ adduct of a polyethyleneamine compound,
providing the product comprising a $CO_2$ adduct of a polyethyleneamine compound to a separation step, which yields a starting material fraction which is provided to the absorption step or to the reaction step, with the remainder being provided to a desorption step, in the desorption step contacting the remainder from the separation step with a stripping gas, and withdrawing a $CO_2$-containing stripping gas from the desorption step and providing it to the absorption step, withdrawing a stripping gas from which $CO_2$ has been absorbed from the absorption step and providing it to the desorption step, providing the product from the desorption step to a further separation step which yields a product fraction of polyethyleneamine compounds which is withdrawn for the separation step, and a fraction comprising $CO_2$ adducts of polyethyleneamine compounds, which is provided to the desorption step or to the reaction step.

* * * * *